United States Patent
Lee et al.

(10) Patent No.: US 11,760,784 B2
(45) Date of Patent: *Sep. 19, 2023

(54) COMPOSITIONS COMPRISING PEDF-DERIVED SHORT PEPTIDES AND USES THEREOF

(71) Applicant: BRIM Biotechnology, Inc., Taipei (TW)

(72) Inventors: Frank Wen-Chi Lee, Bedford, MA (US); Kuanyin Karen Lin, Taipei (TW); Yeou-Ping Tsao, Taipei (TW); Tsung-Chuan Ho, Taipei (TW)

(73) Assignee: BRIM Biotechnology, Inc., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/340,113

(22) PCT Filed: Aug. 24, 2017

(86) PCT No.: PCT/US2017/048340
§ 371 (c)(1),
(2) Date: Apr. 6, 2019

(87) PCT Pub. No.: WO2018/067244
PCT Pub. Date: Apr. 12, 2018

(65) Prior Publication Data
US 2019/0248859 A1    Aug. 15, 2019

Related U.S. Application Data

(60) Provisional application No. 62/405,522, filed on Oct. 7, 2016.

(51) Int. Cl.
| | | |
|---|---|---|
| *C07K 7/08* | (2006.01) | |
| *C07K 14/515* | (2006.01) | |
| *A61K 38/00* | (2006.01) | |
| *A61K 9/06* | (2006.01) | |
| *A61K 9/08* | (2006.01) | |
| *A61K 9/00* | (2006.01) | |
| *A61K 38/55* | (2006.01) | |
| *A61P 27/02* | (2006.01) | |

(52) U.S. Cl.
CPC .......... *C07K 14/515* (2013.01); *A61K 9/0048* (2013.01); *A61K 9/06* (2013.01); *A61K 9/08* (2013.01); *A61K 38/55* (2013.01); *A61P 27/02* (2018.01); *C07K 7/08* (2013.01); *A61K 38/00* (2013.01)

(58) Field of Classification Search
CPC ...... C07K 14/515; C07K 7/08; A61K 9/0048; A61K 9/06; A61K 9/08; A61K 38/00; A61P 27/02
See application file for complete search history.

(56) References Cited

U.S. PATENT DOCUMENTS

| 6,451,763 | B1 * | 9/2002 | Tombran-Tink | ..... | C07K 14/475 |
| | | | | | 514/20.8 |
| 2003/0096750 | A1 * | 5/2003 | Tombran-Tink | ..... | C07K 14/475 |
| | | | | | 514/1.4 |
| 2009/0069241 | A1 * | 3/2009 | Barnstable | ........... | C07K 14/811 |
| | | | | | 514/13.3 |
| 2012/0245097 | A1 * | 9/2012 | Tsao | ........................ | C07K 7/08 |
| | | | | | 514/18.6 |

OTHER PUBLICATIONS

UniProtKB P36955, accessed Feb. 27, 2021 at URL unitprot.org/unitprot/P36955, pp. 1-10 (Year: 2021).*
UniProtKB P97298, accessed Feb. 27, 2021 at URL unitprot.org/unitprot/P97298, pp. 1-10 (Year: 2021).*
Biosynthesis, "N-Terminal Acetylation Amidation Peptides Chemically Synthesized Aminopeptidases Intracellular," 1 page, (2008), accessed Apr. 25, 2018 (Year: 2008).*
Yampolsky et al., "The exchange ability of amino acids and proteins," Genetics, 2005, 170: 1459-1472 (Year: 2005).*
Duh et al., "Vitreous levels of pigment epithelium derived factor in vascular endothelial growth factor: implications for ocular angiogenesis," Am J Ophthalmol 137:668-674 (2004) (Year: 2004).*
Nita et al., "Age-related macular degeneration and changes in the extracellular matrix," Med Sci Monit 20: 1003-1016 (2014) (Year: 2014).*
Hereditary Optic Neuropathies, Merck Manuals, accessed Mar. 27, 2017 at URL merckmanuals.com/professional/eye-disorders/optic-nerve-disorders/hereditary-optic-neuropathies, pp. 1-2 (Year: 2017).*
Fernandes et al., "corneal or epithelial pigment epithelium derived factor is reduced in a Murine model of dry eye disease," ARVO annual meeting abstract, Investigative Ophthalmology & Visual Science 56:335 (Jun. 2015) (Year: 2015).*
Emerson et al., "Emergent therapies for the treatment of neovascular age-related macular degeneration and diabetic macular edema," Biodrugs 21:245-257 (2007) (Year: 2007).*
Diabetic retinopathy, Merck—accessed Jul. 3, 2021 at URL: merckmanuals.com/professional/eye-disorders/retinal-disorders/diabetic-retinopathy?query=ocular neovascular, 5 pages (Year: 2021).*
Introduction to Corneal Disorders, Merck manuals, accessed Sep. 20, 2021 at URL merckmanuals.com/professional/eye-disorders/corneal-disorders/introduction-to-corneal-disorders?query=corneal disorders (Year: 2021).*

(Continued)

*Primary Examiner* — Julie Ha
*Assistant Examiner* — Kristina M Hellman
(74) *Attorney, Agent, or Firm* — Liang Legal Group, PLLC

(57) ABSTRACT

A pharmaceutical composition for treating an ophthalmic disease in a subject includes a peptide and a pharmaceutically acceptable excipient, wherein the peptide contains the sequence of SEQ ID NO: 1: S-X-X-A-X-Q/H-X-X-X-X-I/V-I-X-R, wherein each X is independently any amino acid.

17 Claims, 11 Drawing Sheets

Specification includes a Sequence Listing.

(56) References Cited

OTHER PUBLICATIONS

Lin et al., "dry eye disease: review of diagnostic approaches and treatments," Saudi Journal of ophthalmology 28:173-181 (2014) (Year: 2014).*

Corneal Ulcer, Merck manuals, accessed Sep. 2021 at URL merckmanuals.com/professional/eye-disorders/corneal-disorders/corneal-ulcer (Year: 2021).*

Keratoconus, Merck manuals, accessed Sep. 20, 2021 at URL merckmanuals.com/professional/eye-disorders/corneal-disorders/keratoconus (Year: 2021).*

Nguyen et al., "Unraveling the pathophysiology of Sjogren's syndrome—associated dry eye disease," The Ocular Surface 7: 11-27 (2009) (Year: 2009).*

* cited by examiner

FIG. 5A Cornea

COMPOSITIONS COMPRISING PEDF-DERIVED SHORT PEPTIDES AND USES THEREOF

CROSS REFERENCE TO RELATED APPELLATIONS

This claims the priority of U.S. Application No. 62/405,522, filed on Oct. 7, 2016, the disclosure of which is incorporated by reference in its entirety.

BACKGROUND OF INVENTION

Field of the Invention

The present invention relates to PEDF-derived short peptides and their uses in the treatment and/or amelioration of ophthalmic diseases, particularly dry eye diseases.

Background Art

Dry eye disease or syndromes (DED or DES), also known as Keratoconjunctivitis Sicca, is a complex disease that results in symptoms of discomfort, visual disturbance, and tear film instability which creates potential for damage of the ocular surface. Dry eyes are accompanied by increased osmolality of the tear film and inflammation of the ocular surface. The severity of dry eye signs/symptoms also varies widely among patients. While some patients suffer only minor irritation, others experience significant complications that lead to severe corneal damages and vision impairment.

Dry eye disease (DED) or dry eye syndrome (DES), also known as keratoconjunctivitis sicca, is a multifactorial ocular surface disorder that affects the tear film compositions (lipid, aqueous, and mucin), ocular surface or tear production, resulting in ocular dryness, forging body sensation, irritation and pain. DED can arise from various reasons that affect the production of any of the tear composition or stability of the tear film (e.g., fast evaporation of tears). In addition, tear hyperosmolarity, tear film instability, inadequately support of the ocular surface epithelium integrity can also cause dry eyes.

Tear hyperosmolarity condition can potentially damage and stimulate inflammation cascade of ocular epithelial cells, leading to the loss of surface epithelial cells, including the conjunctival goblet cells. Loss of goblet cells reduces mucin secretion, which subsequently results in loss of protection on surface epithelium and tear film instability, and finally leads to the development of dry eye symptoms as well as damages on corneal epithelial cells. This consequential tear film instability often results in a chronic cycle of inflammation and damage to ocular surface that cause DED.

There is a huge unmet need for the treatment of this multifactorial ocular condition in DED patients. Currently, few therapeutic options are available for DED patients, including artificial tear, anti-inflammation drugs, and analgesics. Even though these treatments can alleviate some symptoms for some patients, better treatment and prevention means for DED are widely desired.

SUMMARY OF THE INVENTION

Embodiments of the current invention relate to reagents and method for the prevention and/or treatment of dry eyes.

One aspect of the invention relates to pharmaceutical compositions for treating an ophthalmic disease in a subject. A pharmaceutical composition according to one embodiment of the invention comprises a peptide and a pharmaceutically acceptable excipient, wherein the peptide comprises the sequence of SEQ ID NO:1: S-X-X-A-X-Q/H-X-X-X-X-I/V-I-X-R, wherein each X is independently any amino acid, provided that the peptide does not comprise the sequence of SLGAEQRTESIIHR (SEQ ID NO:2) or SLGAEHRTESVIHR (SEQ ID NO:3), which correspond to the human and mouse PDSP sequences, respectively. The composition may be in the form of a solution, ointment, or gel.

In accordance with some embodiments of the invention, the peptide comprises the sequences of any one of SEQ ID NO: 6 to 75. In accordance with some embodiments of the invention, the peptide consists of 20, 22, 24, or 29 amino-acid residues in length.

In accordance with some embodiments of the invention, the ophthalmic disease is corneal damage associated disease, which may be dry eye syndrome (DES).

One aspect of the invention relates to methods for treating an ophthalmic disease. A method in accordance with one embodiment of the invention comprises administering to a subject in need thereof a composition containing any one of the above described peptides. The ophthalmic disease is corneal damage associated disease, which may be dry eye syndrome (DES).

Other aspect of the invention will become apparent with the following description and the enclosed drawings.

BRIEF DESCRIPTION OF THE DRAWINGS

5(A) shows representative immunohistochemistry of oxidative stress marker 4-HNE in the corneal epithelia in dry eye.

FIG. 7 shows effects of PDSP on the MMP-9 mRNA expression and activity in NaCl-treated rabbit corneal epithelial cells.

DETAILED DESCRIPTION

Human Pigment Epithelium-derived Factor (PEDF) is a secreted protein containing 418 amino acids, with a molecular weight of about 50 kDa. PEDF is a multifunctional protein with many biological functions (see e.g., U.S. Patent Application Publication No. 2010/0047212). Different peptide regions of the PEDF are found to be responsible for different functions. For example, a 34-mer fragment (residues 44-77 of PEDF) has been identified to have anti-angiogenic activity, while a 44-mer fragment (residues 78-121 of PEDF) has been identified to have neurotrophic properties U.S. Patent Application Publication No. 2010/0047212 discloses that PEDF can promote self-renewal of stem cells. U.S. Pat. Nos. 9,051,547 and 9,617,311 disclose that fragments of PEDF having 20-39 amino acids in length (residues 93-121 of PEDF) can promote stem cells proliferation and wound healing, particularly, proliferation of limbal epithelial stem cells.

Embodiments of the invention relate to short peptide fragments derived from PEDF and their variants. Embodiments of the invention also relate to the uses of these peptides in the prevention and/or treatment of dry eye syndromes (DES).

Dry eye occurs when either the eye does not produce enough tears or when the tears evaporate too quickly. Having dry eyes for a while can lead to abrasion on the surface of the eyes. In advanced cases, the epithelium may undergo pathologic changes, such as squamous metaplasia or loss of goblet cells. In severe cases, patients may end up with cornea damages, including thickening of the corneal surface, corneal erosion, punctate keratopathy, epithelial defects, corneal ulceration, corneal neovascularization, corneal scarring, corneal thinning, and even corneal perforation.

Inventors of the present invention have found that certain peptide fragments derived from PEDF can prevent and/or treat corneal damages caused by dryness.

In an animal model for dry eye diseases, mice were placed in a controlled environment chamber (CEC) to induce dry eyes as previously described (Barabino et al., 2005). Mice placed in the CEC were exposed to a relative humidity (RH)<25%, temperature of 20 to 22° C., with an airflow of 15 L/min, 12 hours per day. Non-Stressed mice were kept in a normal environment (RH >50%, no air flow, temperature of 21-23° C.) for the same duration. After 14 days, non-stressed mice were treated with vehicle, while the stressed mice were treated with either a test peptide (e.g., the 29mer PDSP) or vehicle solution (Vehicle group) for 5 days. Then, the cornea was examined with fluorescein staining.

Figure 1A:
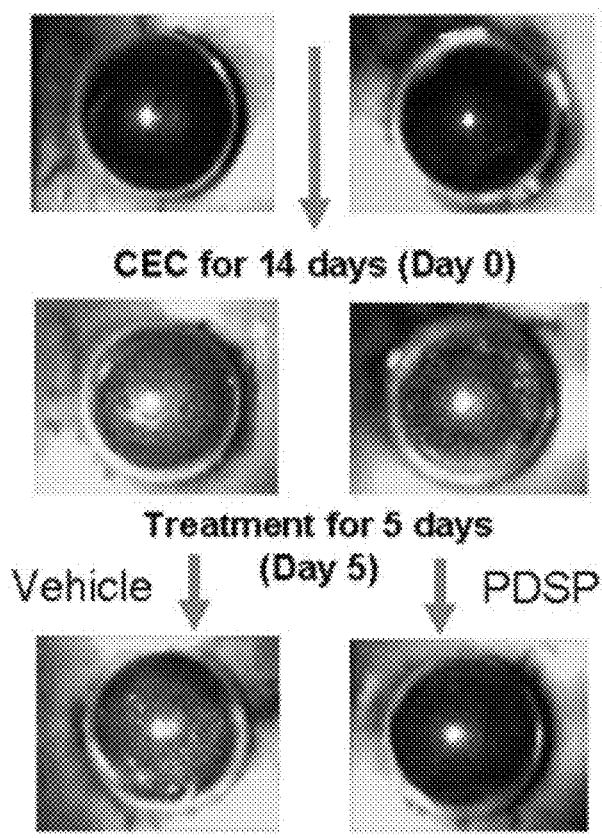
FIG. 1(A) shows effects of PEDF-derived short peptide (PDSP) in desiccating stress-induced dry eye, as revealed by corneal fluorescein staining, which is used to estimate corneal damage. C57BL6 mice were housed in a controlled environment chamber (CEC) for 14 days to induce ocular surface disruption (Day 0) and then treated with PDSP or vehicle for additional 5 days (Day 5).

As shown in FIG. 1(A), at day 14, cornea damages were apparent from fluorescein staining in both the non-stressed and test groups. After treatments with a PEDF-derived short peptide (PDSP, residues 93-121 of PEDF) for 5 days, the damages on the corneal surface were essentially gone, while those in the control group (treatments with vehicle) still exhibited damages in cornea.

Additionally, it is found in the present invention that the PDSPs with various lengths (20-29 amino acids, starting from residue 93 of PEDF) are capable of repairing cornea damages in animal models of dry eye diseases with the concentrations from 10 uM to 200 uM.

Figure 1B:
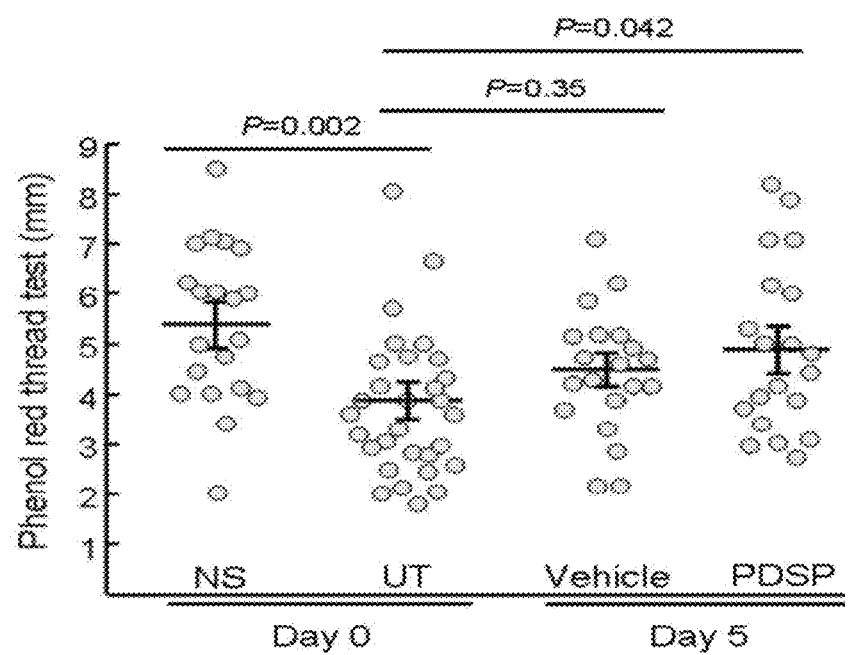
FIG. 1(B) shows amount of aqueous tear production assessed by phenol red thread test. NS: Non-stressed mice housed under normal ambient conditions. UT: untreated mice housed in CEC for 14 days.

FIG. 1(B) shows results of tear production as revealed by phenol red thread test (described in detail in a later section). In FIG. 1(B), NS stands for non-stressed mice, and UT stands for stressed and untreated mice. As shown in FIG. 1(B), treatments with PDSP significantly increased tear production, as compared with the UT and vehicle treated group.

In humans, the tear film coating the eye, known as the precorneal film, has three distinct layers: a lipid layer (secreted by Meibomian glands), an aqueous layer (secreted by lacrimal glands), and a mucous layer (secreted by conjunctival goblet cells). The stress-induced dry eye could result from the reduced production of any or all of these components.

Figure 2A:
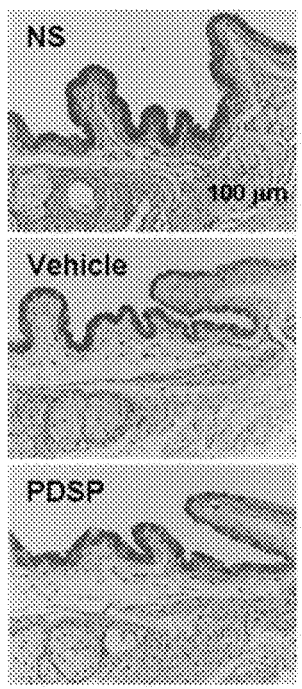
FIG. 2 (A) shows representative images of Periodic Acid Schiff reagent (PAS) staining of goblet cells in the forniceal conjunctiva. Original magnification×100. C57BL6 mice were housed in the CEC for 14 days and then treated with PDSP or vehicle for additional 5 days.
FIG. 2(B) The average number of PAS-stained positive cells was significantly increased after PDSP treatment. The data is presented as the mean±SD.
Figure 2B:
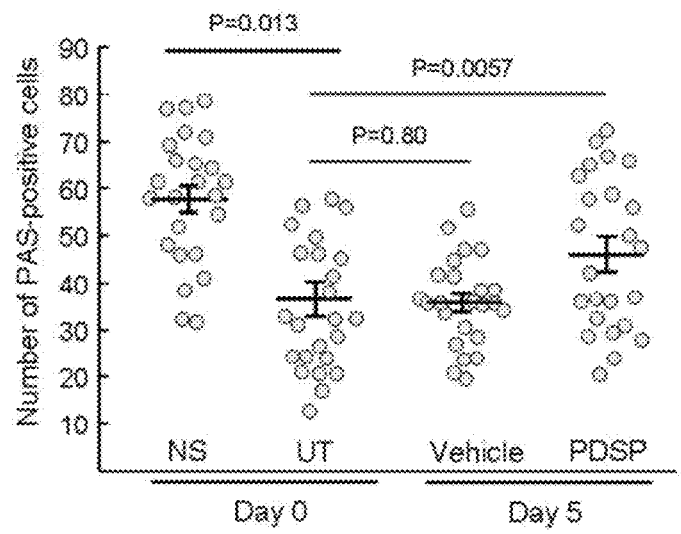

Reduced mucin production could result from reduced goblet cells. The present invention shows that PDSP can prevent the reduction of goblet cells due to dry eye. FIG. 2(A) shows results from period acid Schiff (PAS) reagent staining of mouse eyes. Briefly, C57BL6 mice were housed in CEC for 14 days and then treated with PDSP or vehicle for additional 5 days. Non-stressed eyes are included as non-stressed controls (NS). FIG. 2(A) shows representative staining of goblet cells in a non-stressed eye (NS), a vehicle-treated eye, and a PDSP-treated eye. FIG. 2(B) shows that the PDSP-treated eyes have more goblet cells (more PAS-positive cells), as compared to the untreated stressed eyes and the vehicle-treated eyes.

Figure 3:
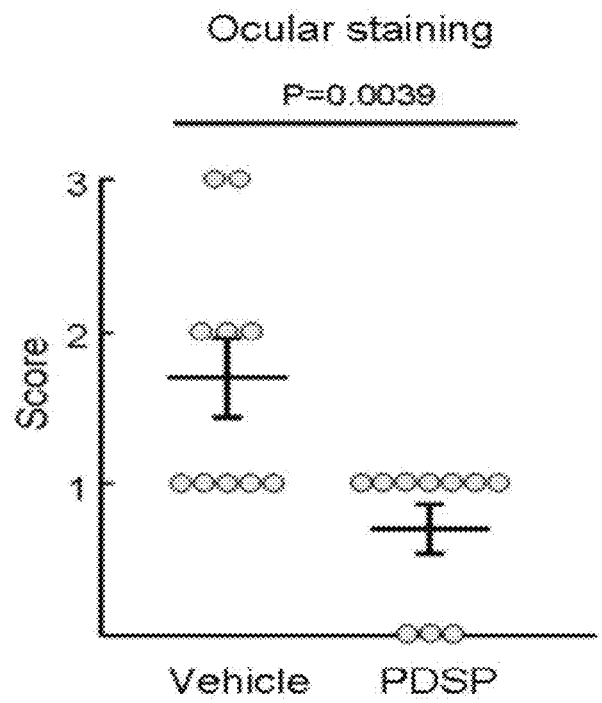
FIG. 3 shows results of topical application PDSP demonstrating the prevention of ocular surface barrier disruption caused by desiccating stress. Mice were housed in the CEC for 14 days and were dosed with 100 μM PDSP starting at the beginning of the housing in CEC. Values are expressed as the mean±SD.

In addition to being able to reverse or cure dry eye syndromes, the inventors also found that the PDSP can prevent damages caused by dry eye conditions. In the experiment, PDSP at the concentration of 100 μM or vehicle (as a control) were applied to eyes of C57BL6 mice and then the mice were kept in controlled environment chamber (with low humidity and airflow) for 14 days. Then, ocular surface barrier disruption caused by desiccating stress was visualized with fluorescein staining. The ocular surface barrier disruption caused by desiccating stress was scored from 0 to 3 based on the extents of ocular surface damages. As shown in FIG. 3, PDSP effectively prevented ocular surface damages, as compared to the vehicle treated group.

Dry eye is associated with abnormalities in the pre-corneal tear film and subsequent inflammatory changes in the entire ocular surface including the adnexa, conjunctiva and cornea. (see, Hessen et al., "Dry eye: An Inflammatory Ocular Disease," J. Ophthalmic Vis. Res., 2014, 9(2): 240-250). Therefore, the effects of PDSPs in corneal inflammatory responses were next examined. Briefly, C57BL6 mice were housed in CEC for 14 days (Day 0) and then treatment with PDSP or vehicle were performed for additional 5 days (Day 5). Then, mRNA levels for inflammatory factors were evaluated by quantitative real-time PCR.

Figure 4:
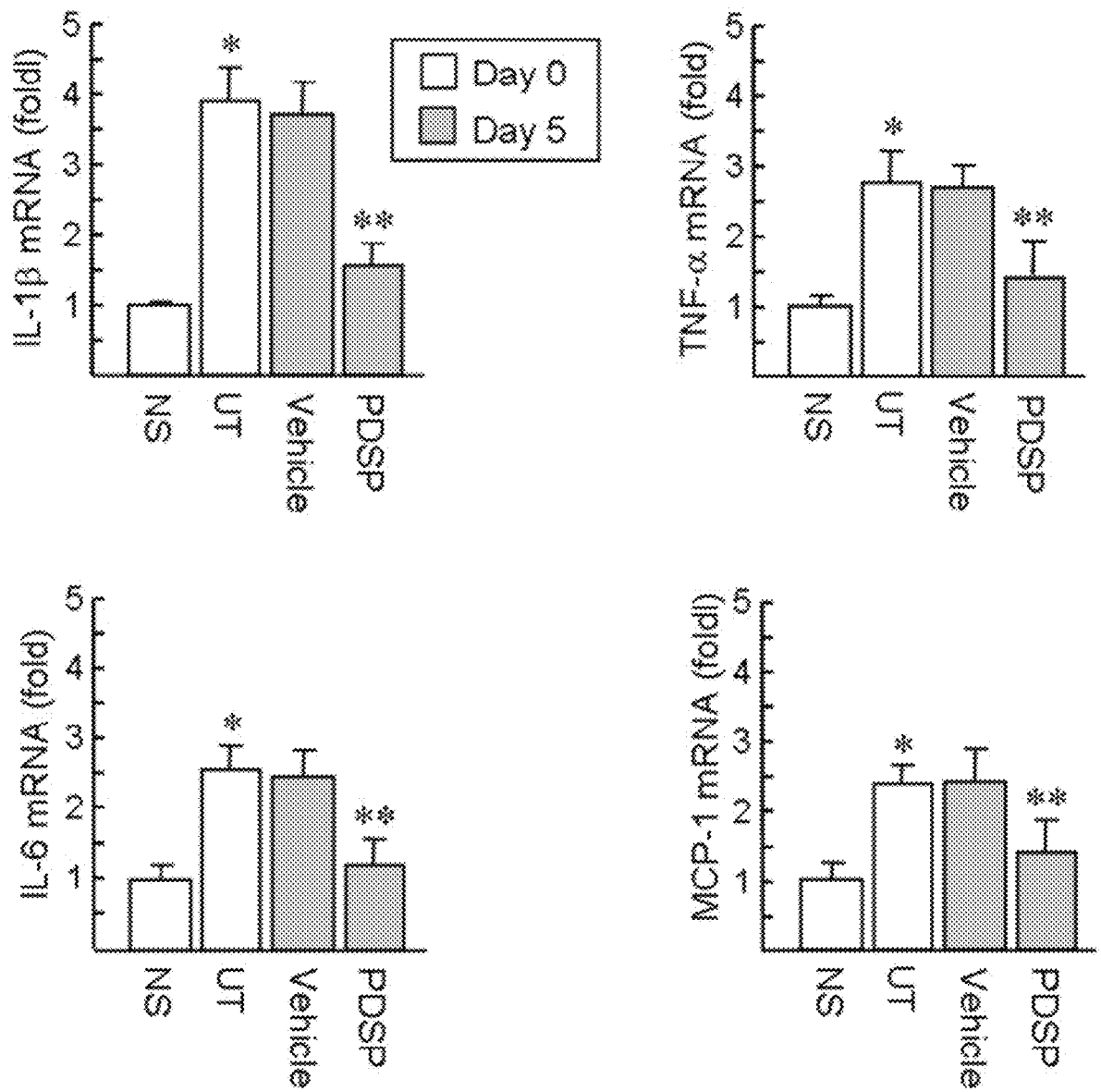
FIG. 4 shows effects of topical PDSP application on desiccating stress-induced ocular inflammation. C57BL6 mice were housed in the CEC for 14 days (Day 0) and then treated with PDSP or vehicle for additional 5 days (Day 5). mRNA levels of various inflammatory factors are evaluated by quantitative real-time PCR. Values are expressed as mean±SE in each group. *$P<0.05$ versus NS: non-stressed mice. **$P<0.05$ versus vehicle-treated group.

As shown in FIG. 4, expression of various inflammation associated factors, e.g., IL-1β, IL-6, TNF-α, and MCP-1 (monocyte chemoattractant protein-1 (MCP-1/CCL2) is a key inflammatory chemokine that controls the recruitment of leukocytes in inflammation and tissue reaction), was increased in stress-induced dry eyes (see the untreated UT group). Treatment with PDSP significantly reduced the expression of these inflammatory factors, as compared with the untreated UT group or the vehicle-treated group. Thus, PDSP can effectively reduce inflammation in stress-induced dry eyes.

In addition, it has been postulated that a relationship exists between dry eye syndrome and the accumulation of oxidative stress. (see, Nakamura et al. Invest. Ophthalmol. Vis. Sci., 2007, 48(4): 1552-8). Therefore, it was also investigated whether PDSP can reduce or prevent oxidative stress in dry eyes.

For this test, mice were housed in CEC for 14 days and the PDSP treatment started at the beginning of housing in CEC. Then, the production of oxidative stress products (e.g., 4-hydroxy-2-nonenal, 4-HNE) was examined. 4-HNE was found throughout animal tissues, and in higher quantities during oxidative stress due to the increase in the lipid peroxidation. 4-HNE contains a reactive aldehyde, which may modify proteins. The 4-HNE-modified proteins may be detected with antibodies specific for the 4-HNE moiety.

Figure 5B:
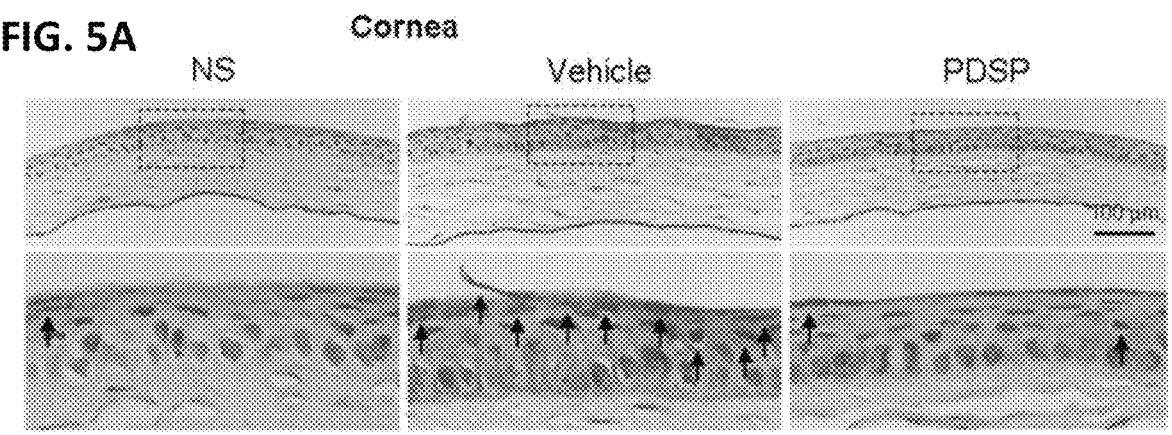
FIG. 5(B) shows results of quantitative analysis of positive 4-HNE cells. Values are expressed as the mean±SD. *P<0.00002 versus vehicle-treated group. (C) Representative immunohistochemistry of o 4-HNE in the conjunctival epithelium in dry eyes.
Figure 5B:
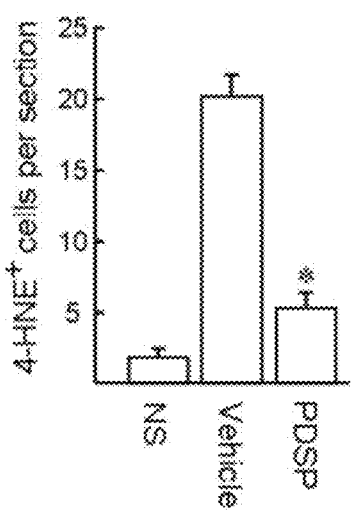
Figure 5C:
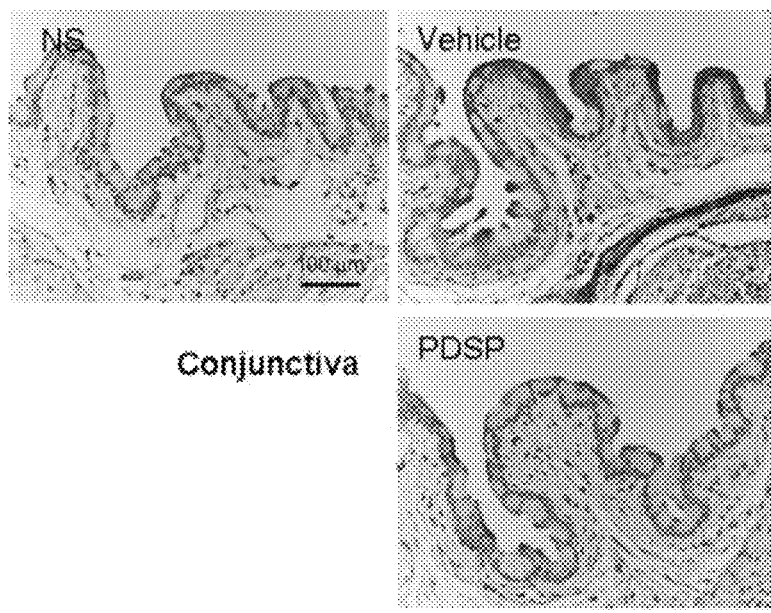
FIG. 5 shows that topical application of PDSP prevents oxidative stress-induced lipid peroxidation. Mice were housed in the CEC for 14 days and were dosed with 100 PDSP starting at the beginning of housing in CEC. FIG.

As shown in FIG. 5(A), non-stressed eyes have minimal 4-HNE. Stress-induced dry eyes have increased 4-HNE staining (the vehicle-treated group). In contrast, PDSP treatment of stress-induced dry eye resulted in significantly reduced production of 4-HNE. FIG. 5 (B) shows results of quantitative analysis of positive 4-HNE cells. FIG. 5(C) shows representative immunohistochemistry staining of 4-HNE in the conjunctival epithelium in dry eyes.

It is generally believed that high osmotic pressure (HOP) of lacrimal fluid is a cause for ocular inflammation and injury. HOP can induce the production of reactive oxygen species (ROS), which are by-products of cellular metabolism. It has been reported that ROS generation is increased in corneal fibroblasts of keratoconus patients and in corneal epithelial cells of dry eye animal models. This observation suggests that ROS may play a role in corneal damages in dry eyes. On the other hand, glutathione (GSH) is a natural species that can counter free radicals or ROS and alleviate or prevent the damages caused by free radicals or ROS.

We therefore examined the effects of PDSP on the intracellular ROS and GSH levels in NaCl-treated (HOP) rabbit corneal epithelial cells. Briefly, rabbit corneal epithelial cells were pretreated with 10 μM PDSP or a negative control peptide (ConP) for 20 hours, followed by treatment with NaCl to induce hyperosmotic stress. After NaCl treatment for another 24 hours, cells were assessed for ROS using a 2',7'-dichlorodihydrofluorescein diacetate ($H_2DCFDA$) probe, which is an ROS indicator dye. $H_2DCFDA$ can diffuse into cells, where its acetate ester linkages are cleaved by intracellular esterases and be oxidized by ROS, which converts the nonfluorescent dichlorodihydrofluorescein diacetate ($H_2DCFDA$) to highly fluorescent 2',7'-dichloro-dihydrofluorescein diacetate (DCF).

Figure 6B:
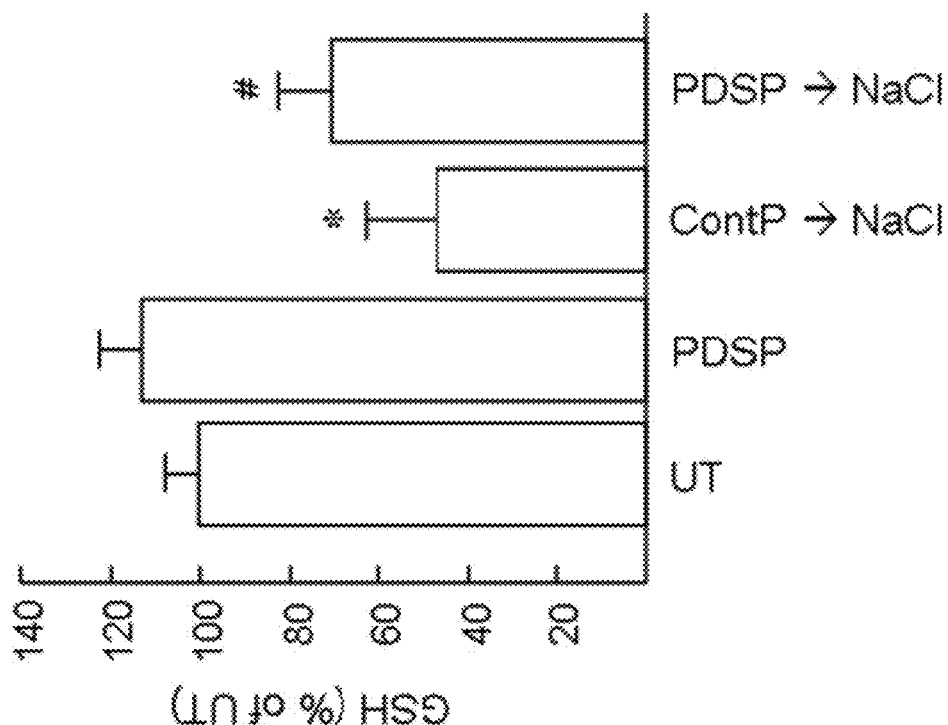
FIG. 6 shows effects of PDSP on the intracellular ROS and GSH levels in NaCl-treated rabbit corneal epithelial cells. Rabbit corneal epithelial cells were pretreated with 10 μM PDSP or a control peptide (ConP, residues 93-110 of PEDF) for 20 hours and then treated with NaCl to induce hyperosmotic stress. After NaCl treatment for further 24 hours, cells were subjected to the detection of ROS by $H_2DCFDA$ probe (A) or glutathione (GSH) by OPA probe (B). *P<0.002 versus untreated cells (cells in isotonic medium). #P<0.05 versus ContP/NaCl-treated cells (cells in hyperosmotic medium).
Figure 6A:
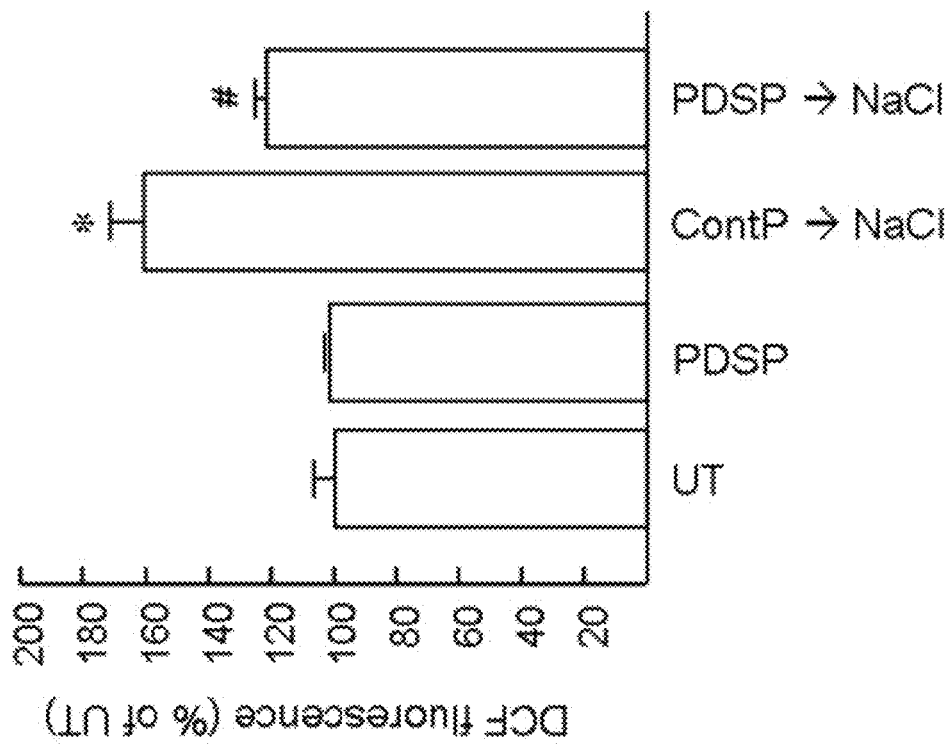

As shown in FIG. 6(A), without HOP, PDSP alone did not increase DCF fluorescence, as compared to the untreated mice. When HOP is induced with NaCl, pretreatment with PDSP resulted in reduced ROS production (i.e., lower DC fluorescence), as compared with pretreatment with the negative control peptide (ConP). This result indicates that PDSP can reduce HOP induced ROS formation.

FIG. 6(B) shows relative GSH levels in different treatment groups. It is interesting that without HOP stress, PDSP alone induced a slight increase in the GSH level, as compared to the untreated mice. This increased level of GSH, an anti-oxidant, would enable the cells to better endure the oxidative stress. Under HOP, PDSP treatment also resulted in increased GSH, as compared with treatments with the control peptide (ConP). These results indicate that PDSP treatments minimize ROS production and at the same time increase the GSH level. The combined effects would render the cells much more tolerant to oxidative stress or hyperosmotic stress.

Dry eye syndrome (DES) includes increased osmolarity of the tear film and inflammation of the ocular surface. Hyperosmolarity of tears contributes to the inflammatory cascade that causes distressed epithelial cells to produce elevated levels of the cytokine MMP-9. Increased MMP-9 activity in dry eyes may contribute to deranged corneal epithelial barrier function, increased corneal epithelial desquamation, and corneal surface irregularity. (Chotikavanich et al., "Production and activity of matrix metalloproteinase-9 on the ocular surface increase in dysfunctional tear syndrome," Invest. Ophthalmol. Vis. Sci. 2009; 50: 3203-3209).

Figure 7A:
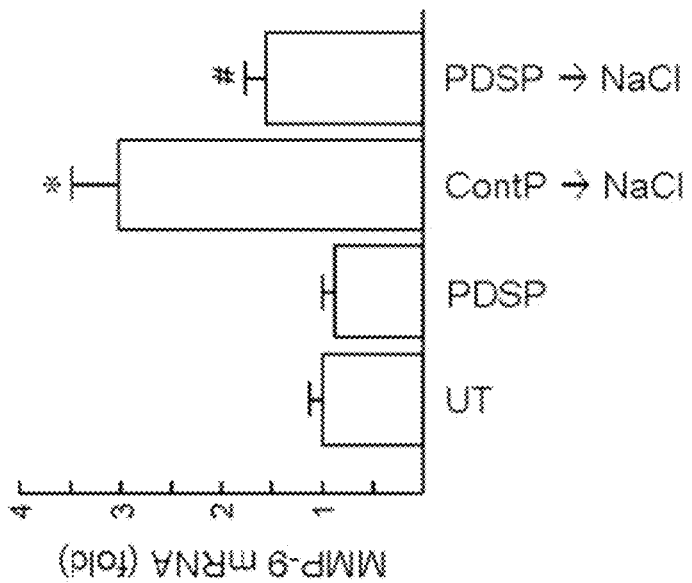
FIG. 7(A) shows MMP-9 mRNA levels, as evaluated by quantitative real-time PCR. Values are expressed as mean±SE in each group. *P<0.005 versus untreated cells. #P<0.02 versus ContP/NaCl-treated cells.
Figure 7B:
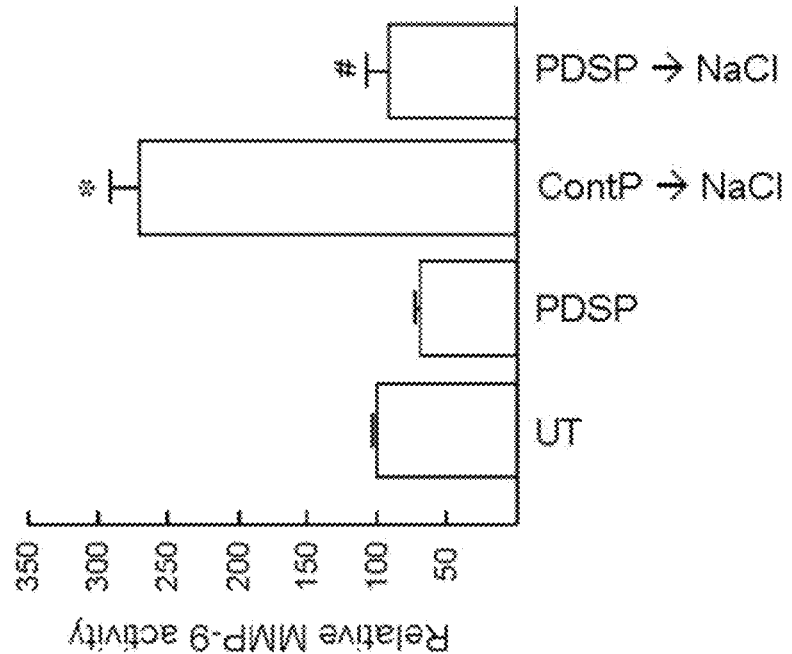
FIG. 7(B) shows MMP-9 activity as evaluated by gelatin zymography. Values are expressed as mean±SE in each group. *P<0.0001 versus untreated cells. #P<0.0003 versus ContP/NaCl-treated cells.

Therefore, we also examined the effects of PDSP on the MMP-9 mRNA expression and activity in NaCl-treated rabbit corneal epithelial cells were treated as described above. FIG. 7(A) shows that without hyperosmotic stress, PDSP alone did not have effect on MMP-9 mRNA levels, as evaluated with quantitative real-time PCR. Hyperosmotic stress induced a substantial (about 2-fold) increase in MMP-9 mRNA level (Negative control peptide, ConP, followed by NaCl treatment). In comparison, PDSP treatment effectively suppressed most of the increase in MMP-9 mRNA level under hyperosmotic stress (PDSP treatment followed with NaCl). The increases in MMP-9 mRNA levels substantially correlate with the expression of the MMP-9 protein as measured with SDS-gel and enzymatic activities, as shown in FIG. 7(B).

The above results clearly show that PDSP of the invention can prevent and treat dry eye diseases (DED) or dry eye syndrome (DES). Specifically, the effects of PDSP of the invention in the prevention and treatment of DED involve: (1) preventing and curing damages to corneal surface induced by dry eye stress; (2) increasing tear production; (3) maintaining or protecting conjunctival goblet cells; (4) suppressing dry eye induced inflammation; (5) alleviating or minimizing oxidative stress induced lipid peroxidation; (6) suppressing the formation of intracellular reactive oxygen species (ROS) and increasing the intracellular glutathione (GSH) levels; and (7) suppressing MMP-9 expression.

Because PDSP of the invention are effective agents for DED prevention and treatments, we further investigated the structure-activity relationship of PDSP by alanine scanning. In the alanine scanning experiments, we use a 29mer from residues 93-121 of human PEDF: $^{93}$SLGAEQR-TESIIHRALYYDLISSPDIHGT$^{121}$ (SEQ ID NO:4). Each of the amino acids in the 29mer was replaced with alanine (or with glycine, if the residue is alanine) and the activities of the alanine-substituted or glycine-substituted mutants were assessed.

Figure 8:
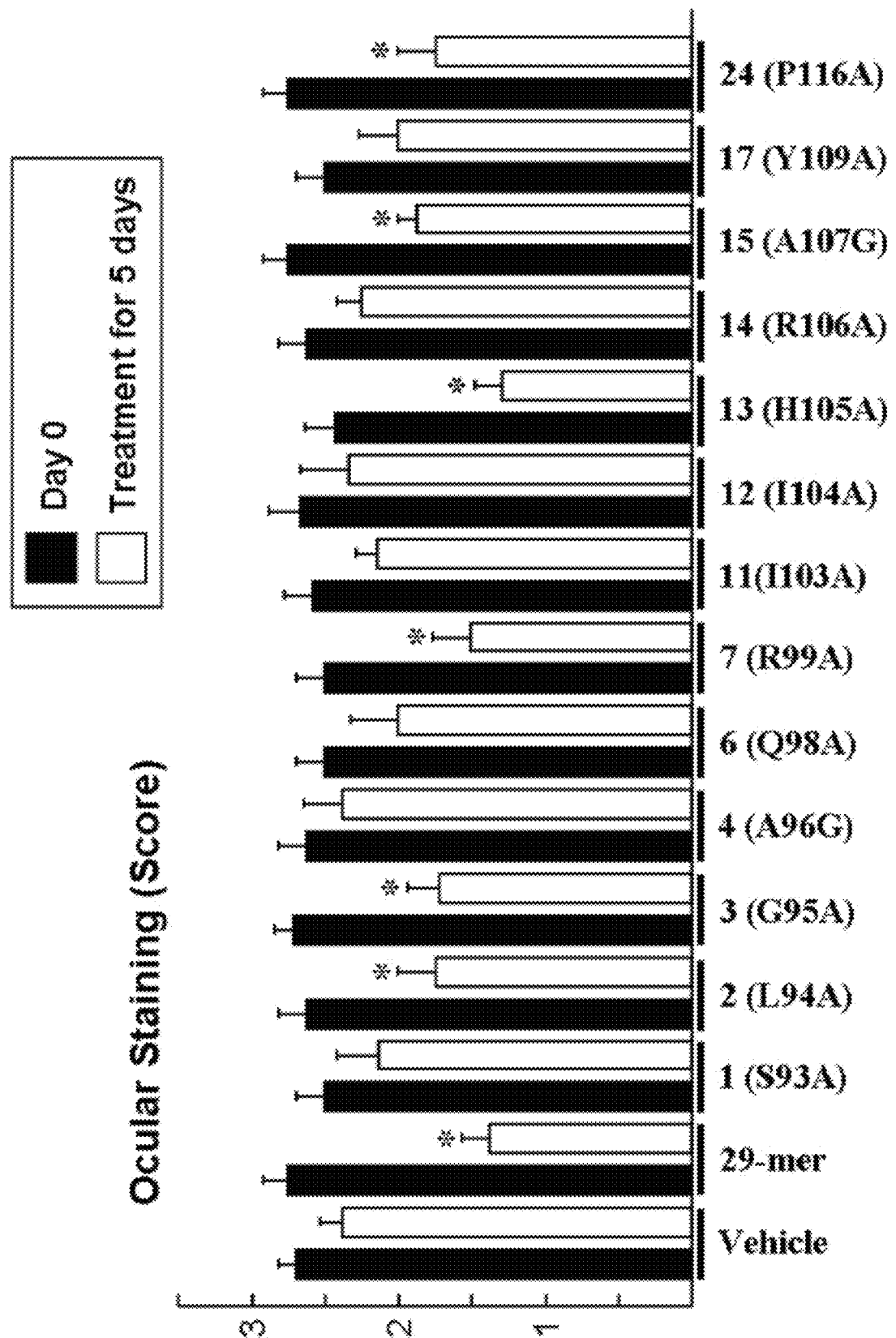
FIG. 8 shows effects of various alanine-substituted peptides in the prevention or treatment of desiccation-induced corneal damages as revealed by fluorescein staining. The mice were housed in the CEC environment for 14 days to induce dry eyes and various peptides were applied on the eyes for 5 days. After 5 days, corneas were stained with fluorescein to assess the damages to the surface.

FIG. 8 shows exemplary results from ocular staining assays. In these tests, desiccation induced corneal surface damages (as assessed with fluorescein staining) were induced in CEC as described above and experimental detailed in a later section. These results show that alanine or glycine substitutions at residues 1 (L93A), 4 (A96G), 6 (Q98A), 11 (I103A), 12 (I104A), and 14 (R106A) in the 29mer resulted in substantial loss of PDSP activity indicating that these residues are essential for the PDSP activity.

Figure 9:
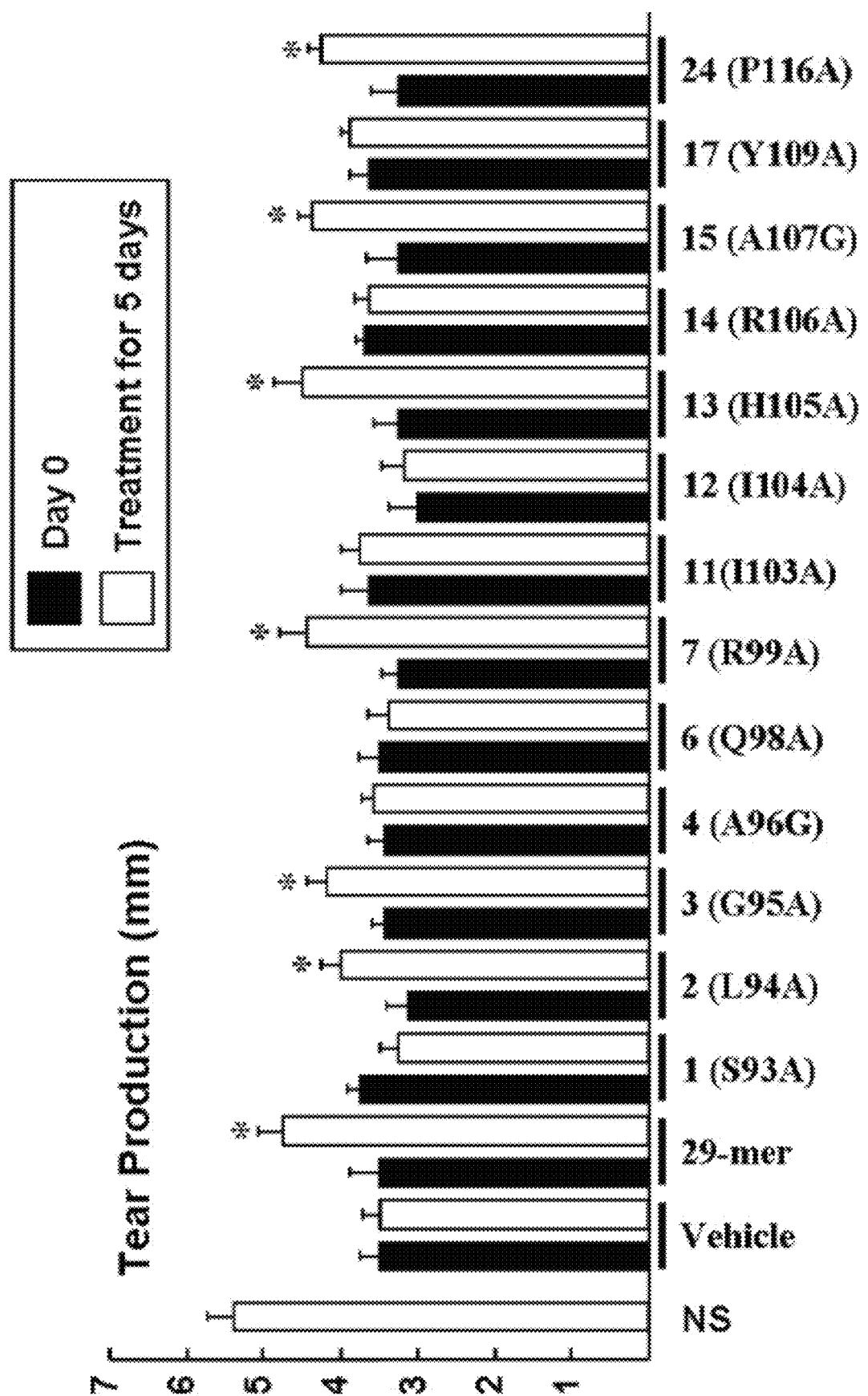
FIG. 9 shows effects of various alanine-substituted peptides in the enhancement of tear productions as revealed by the phenol red thread method.

FIG. 9 shows exemplary results from tear production assays, which were performed as described above and in detail in a following section. The results based on tear production shown in FIG. 9 are consistent with the results based on fluorescein staining shown in FIG. 8. That is, alanine or glycine substitutions at residues 1 (S93A), 4 (A96G), 6 (Q98A), 11 (I103A), 12 (I104A), and 14 (R106A) in the 29mer resulted in substantial losses of abilities of PDSP to induce tear production, indicating that these residues are essential for the PDSP activities.

Figure 10:
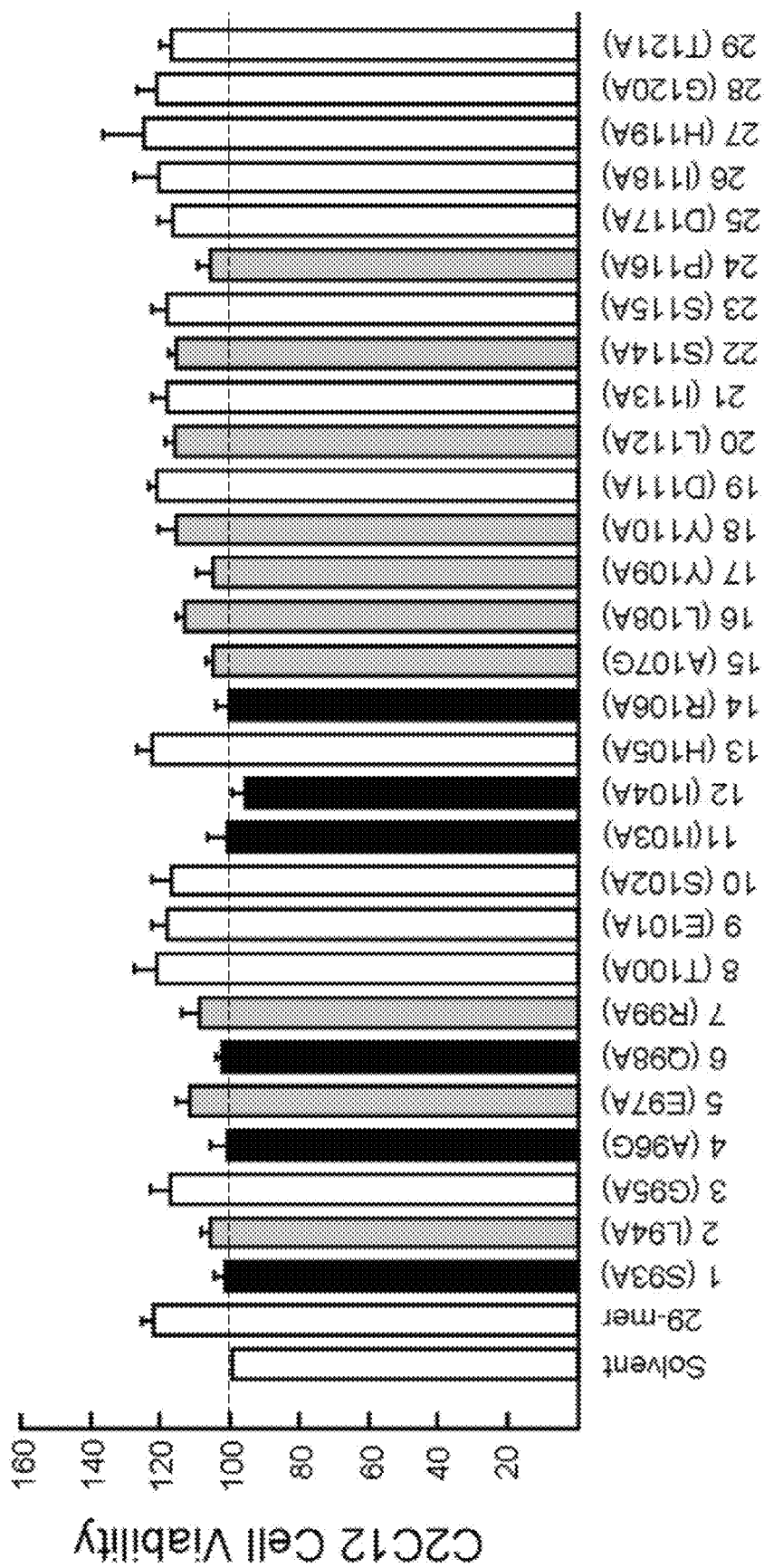
FIG. 10 shows effects of various alanine-substituted peptides on cell viability of C2C12 cells in culture. Cell viabilities were assessed with MTT assay.

The fact that PDSP of the invention can prevent corneal surface damage, reduce oxidative stress in cells, and minimize inflammatory reactions suggests that PDSP may have the ability to maintain cell viability generally. This was tested with cell viability in cell cultures. FIG. 10 shows results of alanine scanning experiments using C2C12 cell cultures. Cell viability may be assessed with staining and cell number counts or with MTT assays. These techniques are well known in the art.

As shown in FIG. 10, alanine (or glycine) substitutions for residues at positions 1 (S93A), 4 (A96G), 6 (Q98A), 11 (I1103A), 12 (I104A), and 14 (R106A) in the 29mer substantially abolished the abilities of these peptides to sustain/enhance viabilities of the cells. These alanine scanning results are consistent with those shown in FIG. 8 and FIG. 9, using dry eye animal models.

Figure 11:
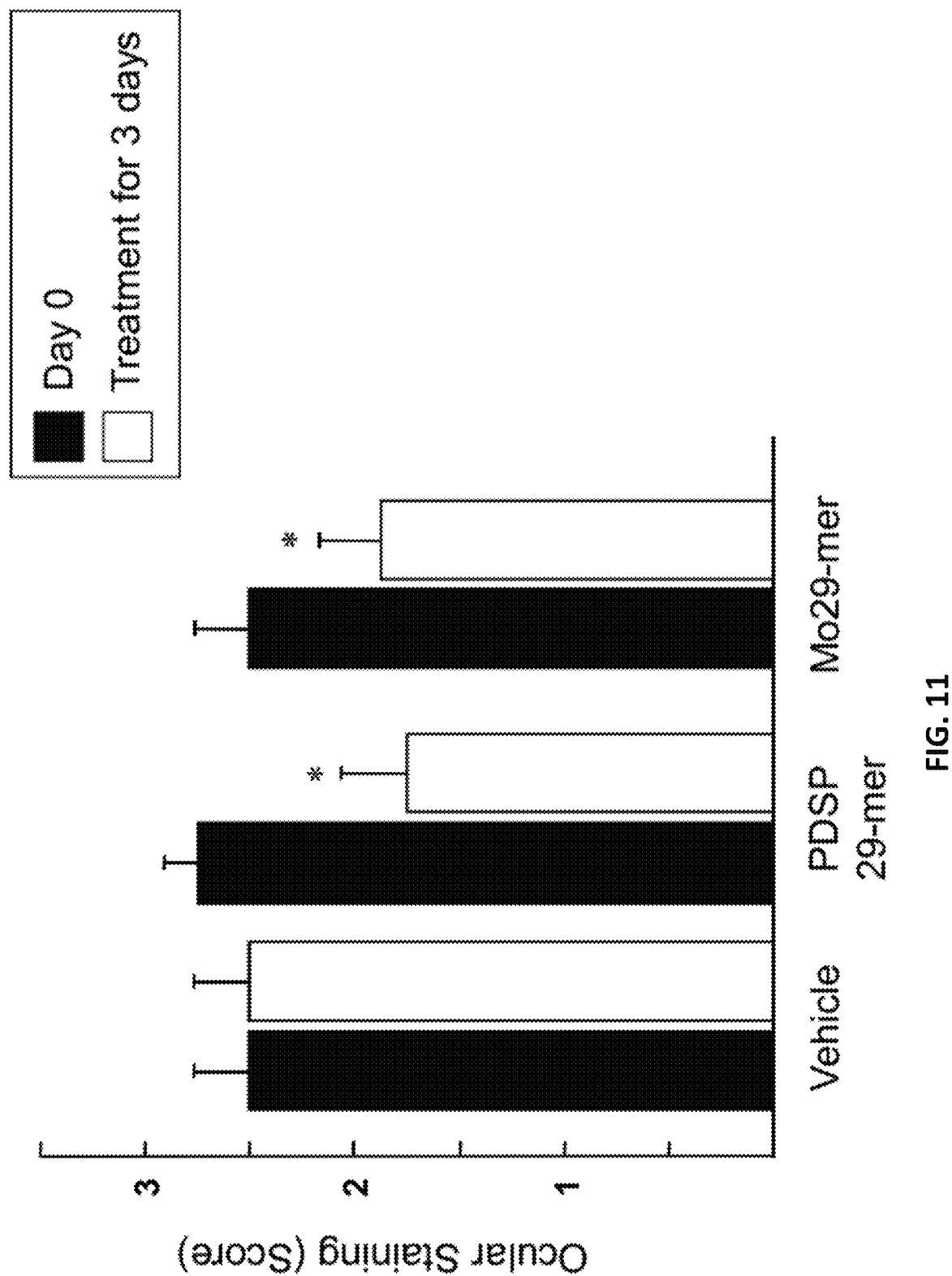
FIG. 11 shows therapeutic effects of human PDSP 29mer and moPDSP 29mer variants in desiccating stress-induced dry eye. C57BL6 mice were housed in a controlled environment chamber (CEC) for 14 days to induce ocular surface disruption (Day 0) and then treatments with peptide or vehicle were started for 3 days (Day 3). Corneal damages were assessed with corneal fluorescein staining. Mean corneal staining score of mice in response to different peptide for 3 days. *P<0.05 versus day 0.
Figure 12:
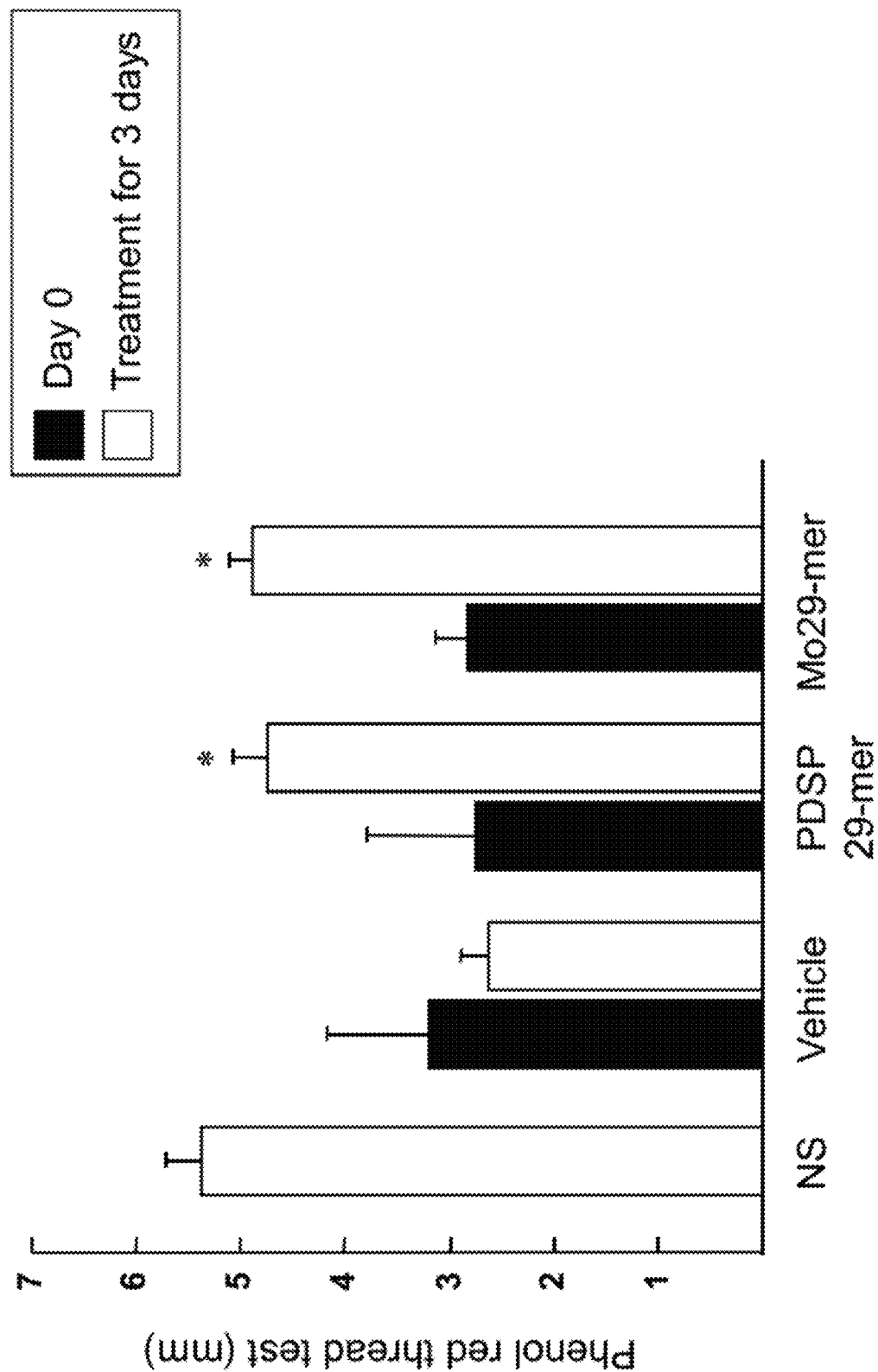
FIG. 12 shows results of tear productions, as assessed with phenol red thread tests. C57BL6 mice were housed in a controlled environment chamber (CEC) for 14 days to induce ocular surface disruption (Day 0) and then treatments with peptide or vehicle were started for 3 days (Day 3). NS: Non-stressed mice housed under normal ambient conditions. *P<0.05 versus day 0.

While the above experiments have been performed with human PDSP sequences (PDSP 29mer: SLGAEQR-TESIIHRALYYDLISSPDIHGT, SEQ ID NO:4), we found that the corresponding mouse sequence (moPDSP 29mer: SLGAEHRTESVIHRALYYDLITNPDIHST, SEQ ID NO:5) function comparably. For example, FIG. 11 shows the results of protection from corneal surface damages induced by desiccation by both the human (PDSP 29mer) and the mouse (moPDSP 29mer), as revealed by ocular staining. It is clear that the mouse sequence has similar effects as that of the human sequence. Similarly, FIG. 12 shows that both human PDSP and mouse PDSP improved tear productions to the same extent. These results confirm that there is no discernable functional difference between human PDSP and mouse PDSP in their abilities to the prevent and/or treat DES.

The amino-acid residue differences between the human PEDF and the mouse PEDF in this region consist of two homologous substitutions, i.e., Q-98 in the human sequence corresponds to H-98 in the mouse sequence and I-103 in the human sequence corresponds to V-103 in the mouse sequence. Therefore, the essential residues at these two locations (98 and 103) may be replaced with the corresponding residues ($^{98}$Q/H and $^{103}$I/V).

One skilled in the art would appreciate that homologous amino-acid substitutions typically do not markedly impact biological activities, even though these two residues are found to be critical for dry eye treatment and prevention. Furthermore, one skilled in the art would appreciate similar homologous substitutions at non-essential positions would be tolerated even better. What amino-acid substitutions are considered homologous are well known in the art. Some examples are: (I, V, L, M), (Q, N, H), (D, E), (R, K, H), (S, T, C), and (F, Y, W), in which the amino acids in the same parenthesis group typically can substitute for one another without significantly impacting the biological activity of a peptide or protein.

Based on these results, one can conclude that an essential peptide sequence for a PDSP to prevent or treat DED may be represented as follows: $^1$S-$^2$X-$^3$X-$^4$A-$^5$X-$^6$Q/H-$^7$X-$^8$X-$^9$X-$^{10\_11}$I/V-$^{12\_13}$X-$^{14}$R (SEQ ID NO: 1), wherein each X denotes a non-essential residue and can be any amino acid, preferably a natural amino acid. The corresponding sequence for human PDSP is: SLGAEQRTESIIHR (SEQ ID NO:2) and that for mouse PDSP is: SLGAEHRTESVIHR (SEQ ID NO:3).

One skilled in the art would appreciate that a peptide comprising these essential residues may be used to prevent or treat dry eyes. Such peptides may be referred to generally as PDSP (i.e., PEDF derived short peptides). Some examples of these PDSP are illustrated in the following TABLE:

| Peptide Sequences | SEQ ID NO |
|---|---|
| $^1$S-$^2$X-$^3$X-$^4$A-$^5$X-$^6$Q/H-$^7$X-$^8$X-$^9$X-$^{10}$X-$^{11}$I/V-$^{12}$I-$^{13}$X-$^{14}$R | 1 |
| $^1$S-$^2$L-$^3$X-$^4$A-$^5$X-$^6$Q/H-$^7$X-$^8$X-$^9$X-$^{10}$X-$^{11}$I/V-$^{12}$I-$^{13}$X-$^{14}$R | 6 |
| $^1$S-$^2$A-$^3$X-$^4$A-$^5$X-$^6$Q/H-$^7$X-$^8$X-$^9$X-$^{10}$X-$^{11}$I/V-$^{12}$I-$^{13}$X-$^{14}$R | 7 |
| $^1$S-$^2$X-$^3$G-$^4$A-$^5$X-$^6$Q/H-$^7$X-$^8$X-$^9$X-$^{10}$X-$^{11}$I/V-$^{12}$I-$^{13}$X-$^{14}$R | 8 |

| Peptide Sequences | SEQ ID NO |
|---|---|
| $^1$S-$^2$X-$^3$A-$^4$A-$^5$X-$^6$Q/H-$^7$X-$^8$X-$^9$X-$^{10}$X-$^{11}$I/V-$^{12}$I-$^{13}$X-$^{14}$R | 9 |
| $^1$S-$^2$X-$^3$X-$^4$A-$^5$E-$^6$Q/H-$^7$X-$^8$X-$^9$X-$^{10}$X-$^{11}$I/V-$^{12}$I-$^{13}$X-$^{14}$R | 10 |
| $^1$S-$^2$X-$^3$X-$^4$A-$^5$A-$^6$Q/H-$^7$X-$^8$X-$^9$X-$^{10}$X-$^{11}$I/V-$^{12}$I-$^{13}$X-$^{14}$R | 11 |
| $^1$S-$^2$X-$^3$X-$^4$A-$^5$X-$^6$Q/H-$^7$R-$^8$X-$^9$X-$^{10}$X-$^{11}$I/V-$^{12}$I-$^{13}$X-$^{14}$R | 12 |
| $^1$S-$^2$L-$^3$X-$^4$A-$^5$X-$^6$Q/H-$^7$A-$^8$X-$^9$X-$^{10}$X-$^{11}$I/V-$^{12}$I-$^{13}$X-$^{14}$R | 13 |
| $^1$S-$^2$A-$^3$X-$^4$A-$^5$X-$^6$Q/H-$^7$X-$^8$T-$^9$X-$^{10}$X-$^{11}$I/V-$^{12}$I-$^{13}$X-$^{14}$R | 14 |
| $^1$S-$^2$X-$^3$G-$^4$A-$^5$X-$^6$Q/H-$^7$X-$^8$A-$^9$E-$^{10}$X-$^{11}$I/V-$^{12}$I-$^{13}$X-$^{14}$R | 15 |
| $^1$S-$^2$X-$^3$A-$^4$A-$^5$X-$^6$Q/H-$^7$X-$^8$X-$^9$A-$^{10}$X-$^{11}$I/V-$^{12}$I-$^{13}$X-$^{14}$R | 16 |
| $^1$S-$^2$X-$^3$X-$^4$A-$^5$E-$^6$Q/H-$^7$X-$^8$X-$^9$X-$^{10}$S-$^{11}$I/V-$^{12}$I-$^{13}$X-$^{14}$R | 17 |
| $^1$S-$^2$X-$^3$X-$^4$A-$^5$A-$^6$Q/H-$^7$X-$^8$X-$^9$X-$^{10}$A-$^{11}$I/V-$^{12}$I-$^{13}$X-$^{14}$R | 18 |
| $^1$S-$^2$X-$^3$X-$^4$A-$^5$X-$^6$Q/H-$^7$X-$^8$X-$^9$X-$^{10}$X-$^{11}$I/V-$^{12}$I-$^{13}$H-$^{14}$R | 19 |
| $^1$S-$^2$X-$^3$X-$^4$A-$^5$X-$^6$Q/H-$^7$X-$^8$X-$^9$X-$^{10}$X-$^{11}$I/V-$^{12}$I-$^{13}$A-$^{14}$R | 20 |
| $^1$S-$^2$L-$^3$G-$^4$A-$^5$X-$^6$Q/H-$^7$X-$^8$X-$^9$X-$^{10}$X-$^{11}$I/V-$^{12}$I-$^{13}$X-$^{14}$R | 21 |
| $^1$S-$^2$L-$^3$G-$^4$A-$^5$E-$^6$Q/H-$^7$X-$^8$X-$^9$X-$^{10}$X-$^{11}$I/V-$^{12}$I-$^{13}$X-$^{14}$R | 22 |
| $^1$S-$^2$L-$^3$G-$^4$A-$^5$A-$^6$Q/H-$^7$X-$^8$X-$^9$X-$^{10}$X-$^{11}$I/V-$^{12}$I-$^{13}$X-$^{14}$R | 23 |
| $^1$S-$^2$L-$^3$G-$^4$A-$^5$X-$^6$Q/H-$^7$R-$^8$X-$^9$X-$^{10}$X-$^{11}$I/V-$^{12}$I-$^{13}$X-$^{14}$R | 24 |
| $^1$S-$^2$L-$^3$G-$^4$A-$^5$X-$^6$Q/H-$^7$A-$^8$X-$^9$X-$^{10}$X-$^{11}$I/V-$^{12}$I-$^{13}$X-$^{14}$R | 25 |
| $^1$S-$^2$L-$^3$G-$^4$A-$^5$X-$^6$Q/H-$^7$X-$^8$T-$^9$X-$^{10}$X-$^{11}$I/V-$^{12}$I-$^{13}$X-$^{14}$R | 26 |
| $^1$S-$^2$L-$^3$G-$^4$A-$^5$X-$^6$Q/H-$^7$X-$^8$A-$^9$E-$^{10}$X-$^{11}$I/V-$^{12}$I-$^{13}$X-$^{14}$R | 27 |
| $^1$S-$^2$L-$^3$G-$^4$A-$^5$X-$^6$Q/H-$^7$X-$^8$X-$^9$A-$^{10}$X-$^{11}$I/V-$^{12}$I-$^{13}$X-$^{14}$R | 28 |
| $^1$S-$^2$L-$^3$G-$^4$A-$^5$X-$^6$Q/H-$^7$X-$^8$X-$^9$X-$^{10}$S-$^{11}$I/V-$^{12}$I-$^{13}$X-$^{14}$R | 29 |
| $^1$S-$^2$L-$^3$G-$^4$A-$^5$X-$^6$Q/H-$^7$X-$^8$X-$^9$X-$^{10}$A-$^{11}$I/V-$^{12}$I-$^{13}$X-$^{14}$R | 30 |
| $^1$S-$^2$L-$^3$G-$^4$A-$^5$X-$^6$Q/H-$^7$X-$^8$X-$^9$X-$^{10}$S-$^{11}$I/V-$^{12}$I-$^{13}$H-$^{14}$R | 31 |
| $^1$S-$^2$L-$^3$G-$^4$A-$^5$X-$^6$Q/H-$^7$X-$^8$X-$^9$X-$^{10}$A-$^{11}$I/V-$^{12}$I-$^{13}$A-$^{14}$R | 32 |
| $^1$S-$^2$L-$^3$G-$^4$A-$^5$E-$^6$Q/H-$^7$X-$^8$X-$^9$X-$^{10}$X-$^{11}$I/V-$^{12}$I-$^{13}$X-$^{14}$R | 33 |
| $^1$S-$^2$L-$^3$G-$^4$A-$^5$E-$^6$Q/H-$^7$R-$^8$X-$^9$X-$^{10}$X-$^{11}$I/V-$^{12}$I-$^{13}$X-$^{14}$R | 34 |
| $^1$S-$^2$L-$^3$G-$^4$A-$^5$E-$^6$Q/H-$^7$A-$^8$X-$^9$X-$^{10}$X-$^{11}$I/V-$^{12}$I-$^{13}$X-$^{14}$R | 35 |
| $^1$S-$^2$L-$^3$G-$^4$A-$^5$E-$^6$Q/H-$^7$X-$^8$T-$^9$X-$^{10}$X-$^{11}$I/V-$^{12}$I-$^{13}$X-$^{14}$R | 36 |
| $^1$S-$^2$L-$^3$G-$^4$A-$^5$E-$^6$Q/H-$^7$X-$^8$A-$^9$E-$^{10}$X-$^{11}$I/V-$^{12}$I-$^{13}$X-$^{14}$R | 37 |
| $^1$S-$^2$L-$^3$G-$^4$A-$^5$E-$^6$Q/H-$^7$X-$^8$X-$^9$A-$^{10}$X-$^{11}$I/V-$^{12}$I-$^{13}$X-$^{14}$R | 38 |
| $^1$S-$^2$L-$^3$G-$^4$A-$^5$E-$^6$Q/H-$^7$X-$^8$X-$^9$X-$^{10}$S-$^{11}$I/V-$^{12}$I-$^{13}$X-$^{14}$R | 39 |
| $^1$S-$^2$L-$^3$G-$^4$A-$^5$E-$^6$Q/H-$^7$X-$^8$X-$^9$X-$^{10}$A-$^{11}$I/V-$^{12}$I-$^{13}$X-$^{14}$R | 40 |
| $^1$S-$^2$L-$^3$G-$^4$A-$^5$E-$^6$Q/H-$^7$X-$^8$X-$^9$X-$^{10}$S-$^{11}$I/V-$^{12}$I-$^{13}$H-$^{14}$R | 41 |
| $^1$S-$^2$L-$^3$G-$^4$A-$^5$E-$^6$Q/H-$^7$X-$^8$X-$^9$X-$^{10}$A-$^{11}$I/V-$^{12}$I-$^{13}$A-$^{14}$R | 42 |
| $^1$S-$^2$L-$^3$G-$^4$A-$^5$E-$^6$Q/H-$^7$R-$^8$X-$^9$X-$^{10}$X-$^{11}$I/V-$^{12}$I-$^{13}$X-$^{14}$R | 43 |
| $^1$S-$^2$L-$^3$G-$^4$A-$^5$E-$^6$Q/H-$^7$X-$^8$T-$^9$X-$^{10}$X-$^{11}$I/V-$^{12}$I-$^{13}$X-$^{14}$R | 44 |
| $^1$S-$^2$L-$^3$G-$^4$A-$^5$E-$^6$Q/H-$^7$R-$^8$A-$^9$E-$^{10}$X-$^{11}$I/V-$^{12}$I-$^{13}$X-$^{14}$R | 45 |
| $^1$S-$^2$L-$^3$G-$^4$A-$^5$E-$^6$Q/H-$^7$R-$^8$X-$^9$A-$^{10}$X-$^{11}$I/V-$^{12}$I-$^{13}$X-$^{14}$R | 46 |
| $^1$S-$^2$L-$^3$G-$^4$A-$^5$E-$^6$Q/H-$^7$R-$^8$X-$^9$X-$^{10}$S-$^{11}$I/V-$^{12}$I-$^{13}$X-$^{14}$R | 47 |
| $^1$S-$^2$L-$^3$G-$^4$A-$^5$E-$^6$Q/H-$^7$R-$^8$X-$^9$X-$^{10}$A-$^{11}$I/V-$^{12}$I-$^{13}$X-$^{14}$R | 48 |
| $^1$S-$^2$L-$^3$G-$^4$A-$^5$E-$^6$Q/H-$^7$R-$^8$X-$^9$X-$^{10}$S-$^{11}$I/V-$^{12}$I-$^{13}$H-$^{14}$R | 49 |
| $^1$S-$^2$L-$^3$G-$^4$A-$^5$E-$^6$Q/H-$^7$R-$^8$X-$^9$X-$^{10}$A-$^{11}$I/V-$^{12}$I-$^{13}$A-$^{14}$R | 50 |
| $^1$S-$^2$L-$^3$G-$^4$A-$^5$E-$^6$Q/H-$^7$R-$^8$T-$^9$X-$^{10}$X-$^{11}$I/V-$^{12}$I-$^{13}$X-$^{14}$R | 51 |
| $^1$S-$^2$L-$^3$G-$^4$A-$^5$E-$^6$Q/H-$^7$R-$^8$T-$^9$E-$^{10}$X-$^{11}$I/V-$^{12}$I-$^{13}$X-$^{14}$R | 52 |
| $^1$S-$^2$L-$^3$G-$^4$A-$^5$E-$^6$Q/H-$^7$R-$^8$T-$^9$A-$^{10}$X-$^{11}$I/V-$^{12}$I-$^{13}$X-$^{14}$R | 53 |
| $^1$S-$^2$L-$^3$G-$^4$A-$^5$E-$^6$Q/H-$^7$R-$^8$T-$^9$X-$^{10}$S-$^{11}$I/V-$^{12}$I-$^{13}$X-$^{14}$R | 54 |
| $^1$S-$^2$L-$^3$G-$^4$A-$^5$E-$^6$Q/H-$^7$R-$^8$T-$^9$X-$^{10}$A-$^{11}$I/V-$^{12}$I-$^{13}$X-$^{14}$R | 55 |
| $^1$S-$^2$L-$^3$G-$^4$A-$^5$E-$^6$Q/H-$^7$R-$^8$T-$^9$X-$^{10}$S-$^{11}$I/V-$^{12}$I-$^{13}$H-$^{14}$R | 56 |
| $^1$S-$^2$L-$^3$G-$^4$A-$^5$E-$^6$Q/H-$^7$R-$^8$T-$^9$X-$^{10}$A-$^{11}$I/V-$^{12}$I-$^{13}$A-$^{14}$R | 57 |
| $^1$S-$^2$L-$^3$G-$^4$A-$^5$E-$^6$Q/H-$^7$R-$^8$T-$^9$E-$^{10}$S-$^{11}$I/V-$^{12}$I-$^{13}$X-$^{14}$R | 58 |
| $^1$S-$^2$L-$^3$G-$^4$A-$^5$E-$^6$Q/H-$^7$R-$^8$T-$^9$E-$^{10}$A-$^{11}$I/V-$^{12}$I-$^{13}$X-$^{14}$R | 59 |
| $^1$S-$^2$L-$^3$G-$^4$A-$^5$E-$^6$Q/H-$^7$R-$^8$T-$^9$E-$^{10}$X-$^{11}$I/V-$^{12}$I-$^{13}$H-$^{14}$R | 60 |
| $^1$S-$^2$L-$^3$G-$^4$A-$^5$E-$^6$Q/H-$^7$R-$^8$T-$^9$E-$^{10}$X-$^{11}$I/V-$^{12}$I-$^{13}$A-$^{14}$R | 61 |
| $^1$S-$^2$L-$^3$G-$^4$A-$^5$E-$^6$Q/H-$^7$R-$^8$T-$^9$E-$^{10}$S-$^{11}$I/V-$^{12}$I-$^{13}$X-$^{14}$R | 62 |
| $^1$S-$^2$L-$^3$G-$^4$A-$^5$E-$^6$Q/H-$^7$R-$^8$T-$^9$E-$^{10}$S-$^{11}$I/V-$^{12}$I-$^{13}$A-$^{14}$R | 63 |
| $^1$S-$^2$L-$^3$G-$^4$A-$^5$E-$^6$Q/H-$^7$R-$^8$T-$^9$X-$^{10}$S-$^{11}$I/V-$^{12}$I-$^{13}$H-$^{14}$R | 64 |
| $^1$S-$^2$L-$^3$G-$^4$A-$^5$E-$^6$Q/H-$^7$R-$^8$T-$^9$A-$^{10}$S-$^{11}$I/V-$^{12}$I-$^{13}$H-$^{14}$R | 65 |
| $^1$S-$^2$L-$^3$G-$^4$A-$^5$E-$^6$Q/H-$^7$R-$^8$X-$^9$E-$^{10}$S-$^{11}$I/V-$^{12}$I-$^{13}$H-$^{14}$R | 66 |
| $^1$S-$^2$L-$^3$G-$^4$A-$^5$E-$^6$Q/H-$^7$R-$^8$A-$^9$E-$^{10}$S-$^{11}$I/V-$^{12}$I-$^{13}$H-$^{14}$R | 67 |
| $^1$S-$^2$L-$^3$G-$^4$A-$^5$E-$^6$Q/H-$^7$X-$^8$T-$^9$E-$^{10}$S-$^{11}$I/V-$^{12}$I-$^{13}$H-$^{14}$R | 68 |
| $^1$S-$^2$L-$^3$G-$^4$A-$^5$E-$^6$Q/H-$^7$A-$^8$T-$^9$E-$^{10}$S-$^{11}$I/V-$^{12}$I-$^{13}$H-$^{14}$R | 69 |
| $^1$S-$^2$L-$^3$G-$^4$A-$^5$X-$^6$Q/H-$^7$R-$^8$T-$^9$E-$^{10}$S-$^{11}$I/V-$^{12}$I-$^{13}$H-$^{14}$R | 70 |
| $^1$S-$^2$L-$^3$G-$^4$A-$^5$A-$^6$Q/H-$^7$R-$^8$T-$^9$E-$^{10}$S-$^{11}$I/V-$^{12}$I-$^{13}$H-$^{14}$R | 71 |
| $^1$S-$^2$L-$^3$X-$^4$A-$^5$E-$^6$Q/H-$^7$R-$^8$T-$^9$E-$^{10}$S-$^{11}$I/V-$^{12}$I-$^{13}$H-$^{14}$R | 72 |
| $^1$S-$^2$L-$^3$A-$^4$A-$^5$E-$^6$Q/H-$^7$R-$^8$T-$^9$E-$^{10}$S-$^{11}$I/V-$^{12}$I-$^{13}$H-$^{14}$R | 73 |
| $^1$S-$^2$X-$^3$G-$^4$A-$^5$E-$^6$Q/H-$^7$R-$^8$T-$^9$E-$^{10}$S-$^{11}$I/V-$^{12}$I-$^{13}$H-$^{14}$R | 74 |
| $^1$S-$^2$A-$^3$G-$^4$A-$^5$E-$^6$Q/H-$^7$R-$^8$T-$^9$E-$^{10}$S-$^{11}$I/V-$^{12}$I-$^{13}$H-$^{14}$R | 75 |

One skilled in the art would appreciate that the peptide sequences listed in the Table above are for illustration only and other permutations are possible without departing from the scope of the invention. In addition, while the above may represent short or minimal peptides that are effective in preventing and/or treating dry eye syndrome, longer peptides may also be used. In particular, longer peptides may offer more favorable pharmacokinetics and/or bioavailability.

For longer peptides, additional amino acids may be included at the N- and/or C-terminus of any one of the above peptide. The additional amino acids may be any suitable residues, such as those from human or mouse PEDF flanking the regions of the above peptides. Particular examples of longer peptides may include 20mer (residues 93-112 of PEDF; SEQ ID NO:76), 22mer (residues 93-114 of PEDF; SEQ ID NO:77), 24mer (residues 93-116 of PEDF; SEQ ID NO:78), and 29mer (residues 93-121 of PEDF; SEQ ID NO:4).

Embodiments of the invention also relate to methods for preventing and/or treating dry eye in a subject. A subject in accordance with embodiments of the invention may be a human or an animal. A method in accordance with an embodiment of the invention may comprise either administering to a subject in need of dry eye prevention or treatment with a composition comprising a peptide selected from any one described above. In accordance with examples of the invention, the compositions may comprise a peptide of the invention, or a salt of such a peptide, together with a pharmaceutically acceptable carrier or excipient, such as distill water, saline, oil, or gel.

A composition of the invention may be formulated in any suitable dosage forms, such as a solution, an ointment, a suspension, a gel or an emulsion, which may be formulated at any suitable concentrations, such as 10-200 μM. One skilled in the art would be able to formulate these at a suitable concentration to deliver an effective dose without inventive efforts. These dosage forms may be formulated for topical application to the eyes or other suitable routes of administrations (e.g., oral or injection).

Embodiments of the invention will be further illustrated with the following experimental details and examples. One skilled in the art would appreciate that these experimental details and examples are for illustration only and that other modifications and variations are possible without departing from the scope of the invention.

Materials and Methods

Carboxymethylcellulose sodium (CMC), period acid Schiff (PAS) reagent and dexamethasone were all from Sigma-Aldrich (St. Louis, Mo., USA). CMC (1% w/v) in Balance salt solution (BSS; Alcone) was used as vehicle for PDSPs. PDSPs and a negative control peptide (ConP) were synthesized and modified with acetylated at the $NH_2$ termini and amidated at the COOH termini for stability and characterized by mass spectrometry (>95% purity) to order at GenScript (Piscataway, N.J., USA).

Animals

Seven to 8-week-old female C57BL/6 mice were used for these experiments. Experimental procedures were approved by the Mackay Memorial Hospital Review Board and conducted according to the ARVO Statement for the Use of Animals in Ophthalmic and Vision Research.

Dry Eye Model

Dry eye was induced by placing mice in a controlled environment chamber (CEC) as previously described (Barabino et al., 2005). Briefly, mice placed in the CEC were exposed to a relative humidity (RH)<25%, temperature of 20 to 22° C., and airflow of 15 L/min, 12 hours per day. Non-stressed (NS) mice without stress-induced dry eye were kept in a normal environment (RH >50%, no air flow, temperature of 21-23° C.) for the same duration. Corneal fluorescein staining and Animals were anesthetized by an intraperitoneal injection of a mixture of zoletil (6 mg/kg) and xylazine (3 mg/kg). Corneal epithelial injury was determined by staining with topical fluorescein (Fluor-I-Strip, Ayerst Laboratories, Philadelphia, Pa.). Corneal fluorescein staining was examined with a slit-lamp biomicroscope under cobalt blue light and photographed with a digital camera. Dye staining of the cornea was scored in a manner as follows: score 0 for no punctuate staining; score 1 when less than one third of the cornea was stained; score 2 when two thirds or less was stained; and score 3 when more than two thirds was stained (Horwath-Winter J 2013).

Measurement of Tear Production

Tear production was measured with phenol red-impregnated cotton threads (Zone-Quick; Oasis, Glendora, CA). The validity of this test in mice was performed as previously described (Dursun et al., 2002). The threads were held with jeweler forceps and placed in the lateral canthus for 60 seconds. The tear production is expressed in millimeters of thread that is wet by the tear and turned red.

PAS Staining of Goblet Cells

After animals were euthanized, eyes were surgically excised, fixed in 10% formalin, paraffin embedded, and cut into 5-μm sections. The sections were stained with Periodic Acid Schiff reagent (PAS; Sigma-Aldrich) for measuring goblet cells in the superior and inferior conjunctiva and were examined and photographed with a microscope equipped with a digital camera. PAS-positive goblet cells in the conjunctiva were measured in five sections from each eye.

RNA Extraction and Quantitative Real-Time PCR

The total RNA was extracted from cells using TRIzol (Invitrogen) and treated with RNase free DNase I (Qiagen, Santa Clarita, CA) to remove genomic DNA and then purified with an RNA purification kit (Dynabeads; Invitrogen). Synthesis of cDNA was performed by Superscript III (Invitrogen). Quantitative real-time PCR was performed in a GeneAmp 7700 sequence detection system (Applied Biosystems, Foster City, CA). Amplification was carried out in a total volume of 40 μl containing 3 pmol of primers, serially diluted RT product and SYBR Green PCR core reagents (Applied Biosystems). The sequence of specific PCR primers were mouse TNF-α (accession number: NM_013693) sense, 5'-CTACCTTGTTGCCTCCTCTTT-3' (SEQ ID NO:79), antisense, 5'-GAGCAGAGGTTCAGTGATGTAG-3' (SEQ ID NO:80); mouse IL-10 (accession number: NM_008361) sense, 5'-GGTGTGTGACGTTCCCATTA-3' (SEQ ID NO:81), antisense, 5'-ATTGAGGTG-GAGAGCTTTCAG-3' (SEQ ID NO:82); mouse IL-6 (accession number: NM_031168) sense, 5'-GTCTGTAGCT-CATTCTGCTCTG-3' (SEQ ID NO:83), anti-sense, 5'-GAAGGCAACTGGATGGAAGT-3' (SEQ ID NO:84); mouse MCP-1 (accession number: NM_011333) sense, 5'-CTCGGACTGTGATGCCTTAAT-3' (SEQ ID NO:85), anti-sense, 5'-TGGATCCACACCTTGCATTTA-3' (SEQ ID NO:86); rabbit MMP-9 (accession number: NM_001082203) sense, 5'-TGCGAGTTTCCGTT-CATCTT-3' (SEQ ID NO:87), anti-sense, 5'-GTAGAGCTTGTCCTTGTCGTAG-3' (SEQ ID NO:88); The step-cycle program was set for denaturing at 95° C. for 15 s, and annealing and extension at 62° C. for 1 min, for a total of 40 cycles. All determinations were measured in triplicate. The cycle threshold (Ct) values corresponded to the PCR cycle number at which fluorescence emission in real time reaches a threshold above the base-line emission were analyzed using GeneAmp 7700 SDS software. The Ct value of the PCR product of interest and a control mRNA (GAPDH) were then used to calculate relative quantities of mRNA between samples.

Immunohistochemistry

Oxidative stress-induced lipid peroxidation was assessed by immunohistochemical detection of 4-hydroxy-2-nonenal (4HNE) in the cornea and conjunctiva. Formalin-fixed, paraffin-embedded eye specimens were deparaffinized in xylene and rehydrated in a graded series of ethanol concentrations. Slides were blocked with 10% goat serum for 60 min and then incubated with primary antibody against 4-HNE (1:100 dilution) (ab46545, Abcam) 4 hours at room temperature. The slides were subsequently incubated with the appropriate peroxidase-labeled goat immunoglobulin (1:500 dilution; Chemicon, Temecula, Calif.) for 20 min and then incubated with chromogen substrate (3,3'-diaminobenzidine) for 2 min before counterstaining with hematoxylin.

Corneal Epithelial Cell Culture and Treatment

Limbal stem cells were isolated from 6-month-old New Zealand white rabbits and continuously cultivated for 14 days by DMEM/F-12 basal medium based cell-suspension culture to achieve corneal-liked epithelial cell differentiation as previously described (Ho et al., 2013). To induce ROS or MMP-9 activity caused by hyperosmotic stress, cells were incubated overnight in hypertonic media (463 mOsm) achieved by addition of 90 mM NaCl. Cells cultured in DMEM/F-12 basal medium (309 mOsm) was used as negative control. To detect the preventive effect on hyperosmotic stress-induced ROS or MMP-9 activity, cells were pre-treated with 10 µM PDSP for 20 hours before the treatment of NaCl.

Gelatin Zymography

To detect MMP-9 activity, 10 µL of culture medium was used to perform gelatin zymography as previous described method (Li et al., 2004). The band intensity was evaluated in zymography with a model GS-700 imaging densitometer (Bio-Rad Laboratories, Hercules, Calif.) and analyzed using Labworks 4.0 software.

Measurement of Intracellular ROS and Glutathione Content

Intracellular ROS generation was assayed using 2',7'-dichlorodihydrofluorescein diacetate ($H_2$DCFDA; Molecular Probes, Eugene, Oreg.) which, when oxidized by ROS, releases the green fluorescent compound 2',7'-dichlorofluorescein (DCF). To detect ROS by spectrofluorometric assay, the cells were washed with PBS and then lysed by NP-40 lysis buffer (10 mM Tris-Cl, pH 7.4, 10 mM NaCl, and 0.5% NP-40) and incubated with PBS containing 5 µM $H_2$DCFDA in the dark for 15 min at 37° C. Fluorescence (excitation, 488 nm; emission, 520 nm) was measured with a Spectra MAX GEMINI Reader (Molecular Devices, Sunnyvale, Calif., USA). The background fluorescence from control wells without the addition of $H_2$DCFDA was subtracted from the experimental readings.

The GSH levels were quantified using a Glutathione Assay Kit (BioVision Research Products, Mountain View, Calif.) according to the manufacturer's recommendations. In brief, the perchloric acid treated cell lysate was incubated with the OPA (o-phthalaldehyde) probe and GSH buffer for 40 min at room temperature. The fluorescence was read at 340 nm for excitation and 420 nm for emission on a SPECTRAmax GEMINI XS fluorescence microplate spectrophotometer (Molecular Devices, Sunnyvale, Calif.).

Topical PDSP Treatment Restores Ocular Surface Damage Induced by Desiccating Stress To determine whether PDSP have therapeutic effects in a desiccating stress (DS)-induced ocular surface defects, mice were housed at controlled environment chamber (CEC) for 14 days to create ocular surface disruption. After 14 days in CEC, we used mice with fluorescence scores that are above 2 for the first experiments (FIG. 1A). Subsequently, dry eyes were treated topically with PDSP at 25-200 µM (3 times/day) or PDSP vehicle (1% CMC in BSS) for another 5 days while maintaining the same desiccating stress protocol.

On day 0, the mean tear volume significantly decreased in mice compared with non-stressed (NS) mice as measured by a cotton thread test (3.8±0.5 mm versus 5.4±0.4 mm; FIG. 1B). The tear production was significantly increased in the eyes after mice were treated with the PDSP for 5 days (5±0.3 versus 4.5±0.2) compared with the vehicle group.

The PDSP Partially Restores the Amounts of Goblet Cells in the Conjunctiva

Goblet cells are resided mainly in the superficial epithelium of conjunctival fornix and are responsible for mucous tear production. Periodic Acid Schiff (PAS) staining of NS eye showed that goblet cells display a continuous homogeneous pattern at conjunctival epithelium (FIG. 2A). However, 14 days after desiccating stress (Day 0), PAS staining of the conjunctiva showed that the number of goblet cells was markedly decreased as compared to NS group (58±3.1 versus 38±3.2; FIG. 2B). Treatment with PDSP or vehicle in eye drop for 5 days, the conjunctival goblet cell counts were significantly higher in the PDSP-treated eyes, as compared to the vehicle-treated controls (46±3.8 versus 37±1.1). Collectively, the PDSP treatment did rescue the number of goblet cells.

Topical PDSP Prevents Ocular Surface Damage Induced by Desiccating Stress

To investigate whether the PDSP can suppress DS-induced corneal epithelial disruption, we applied the 14-day desiccating stress protocol to mice, and treated these mice topically with PDSP 3 times a day. After 14 days, corneal epithelial defect was assessed by fluorescein dye staining (FIG. 3) and results revealed the corneal fluorescein staining scores were significantly higher in the vehicle-treated eyes, compared to the PDSP-treated eyes (1.7±0.3 versus 0.7±0.2). This result indicates that PDSP can also display preventive effect on ocular surface against desiccating stress.

Comparable Function of Human and Mouse PDSP in the Desiccating Stress Animal Model To investigate whether the same region of PEDF in human and mouse functions comparably in the treatment of DED subject. The activities of human PDSP and murine PDSP were examined in desiccating stress-induced dry eye model in mice. It is shown that the both human and mouse PDSP are capable of restore the ocular surface damages induced by desiccating stress (FIG. 11) as well as the tear production (FIG. 12) in mice with stress-induced dry eyes.

The PDSP Suppresses the Desiccating Stress-Induced Inflammatory Response

It has been suggested that inflammation may increase ocular surface damage in desiccating stress-induced dry eye in experimental animals (Luo et al., 2004; De Paiva et al., 2006). Among the proinflammatory mediators, it was reported that the desiccating stress-induced dry eye was ameliorated in mice pretreated with TNF-α or interleukin-1 (IL-1) blocker [Ji Y W 2013; Okanobo A 2012]. As shown in FIG. 4, after mice being housed in CEC for 14 days (set as day 0; untreated mice), the mRNA levels of proinflammatory mediators, including IL-1β, TNF-α, IL-6 and MCP-1 were significantly up-regulated by 3.9-, 2.8-, 2.6-, and 2.4-fold, respectively, compared to the mice housed at non-stressed (NS) environment. However, topical PDSP treatment for 5 days in mice apparently repressed the mRNA expression of ocular IL-1β, TNF-α, IL-6 and MCP-1 by factors of 2.4-, 1.9-, 2.0- and 1.7-fold, respectively, compared to the vehicle-treated group. Taken together, our results indicate that the PDSP attenuated DS-induced ocular inflammatory responses.

The PDSP Partially Prevents Lipid Peroxidation Related Ocular Surface Damage Oxidative damage at ocular surface that results from reactive oxygen species (ROS) overproduction has been implicated in the pathogenesis of dry eye (Wakamatsu et al., 2013). We investigated whether PDSP can suppress lipid peroxidation related membrane damage through 4-HNE immunohistochemical staining. As shown in FIG. 5A, the 4-HNE staining in the corneal epithelia, after mice being housed in CEC for 14 days, showed nuclear and/or perinuclear localization on wing cells of epithelium, consistent with a previous report (Nakamura et al., 2007). The number of cells positively stained for 4-HNE was 1.9±0.6, 20.1±1.4, and 5.3±1.0 in the NS, vehicle and PDSP groups, respectively (FIG. 5B), indicating that PDSP is capable of preventing lipid peroxidation. In addition, DS-induced lipid peroxidation in the conjunctiva was also assessed by 4-HNE staining and immunohistochemical staining results showed that the 4-HNE signal was clearly stronger in vehicle-treated eyes than in eyes subjected to the PDSP treatment, further supporting the finding in the anti-oxidative effect of PDSP (FIG. 5C). Collectively, PDSP treatment significantly suppressed DS-induced oxidative damage in ocular surface.

The PDSP Prevents Hyperosmotic Stress-Induced ROS Accumulation and Glutathione Depletion in Corneal Epithelial Cells Elevated tear osmolarity is thought to be a core mechanism in the dry eye to induce inflammation and ocular surface damage (Stahl et al., 2012). The current cutoff for a dry eye diagnosis is 316 mOsm compared to 300-310 mOsm in normal eyes (Liu et al., 2009). However, in vitro studies of hyperosmolarity in corneal epithelial cells, long-term exposure of the cells to higher levels of tear osmolarity (350-500 mOsm) is required to induce the ROS and MMP-9 activity (Li D Q 2004; Li J 2016).

To investigate the effect of hyperosmotic stress on the intracellular ROS formation, rabbit corneal epithelial cells were cultured in a hyperosmotic medium (463 mOsM) by adding 90 mM NaCl for 24 hours. The intracellular ROS levels were detected by $H_2DCFDA$ probe and measured the formation of DCF-fluorescence by spectrofluorometer.

As shown in FIG. 6A, the DCF-fluorescence increased 1.6-fold after cells cultured in hyperosmotic medium for 24 hours, compared to cells cultured in isotonic medium (309 mOsm). However, the rabbit corneal epithelial cells that were pretreated with PDSP showed suppressed DCF-fluorescence level by a factor of 1.3-fold, as compared to cells that were treated with NaCl alone ($P<0.04$). Control peptide (ContP) pretreatment had no such effects. NaCl-induced hyperosmotic stress also markedly depleted the levels of glutathione (GSH), an antioxidant, in comparison to the control cells in isotonic environment (FIG. 6B; 46.715.4% versus 100-7.0%), whereas cells retreated with the PDSP significantly increased the GSH levels up to 70.511.4%. These results indicate that the PDSP has an anti-oxidative effect in corneal epithelial cells that are treated with NaCl-induced hyperosmotic stress (463 mOsM), at least partially via enhancing GSH levels.

The PDSP Suppresses Hyperosmotic Stress-Induced MMP-9 Expression in Corneal Epithelial Cells To investigate the effect of PDSP on hyperosmotic stress-induced MMP-9 expression in corneal epithelial cells, cells were pretreated with the PDSP or control peptide (ConP) for 20 hours and then exposed the cells to hyperosmotic medium (463 mOsM) for another 24 hours. As shown in FIG. 7A, the mRNA level of MMP-9 in cells treated with ContP/hyperosmotic medium was significantly up-regulated by 3-fold, as compared to the cell cultured in isotonic medium (untreated control). However, the PDSP pretreatment repressed the MMP-9 mRNA expression by a factor of 2-fold.

Gelatin zymography also demonstrated that the hyperosmotic stress induced MMP-9 activity by 2.7-fold, as compared to untreated control (size near 90 kDa; FIG. 7B). The zymography further showed that the PDSP pretreatment repressed the MMP-9 activity by 3-fold. These results indicate that PDSP suppresses MMP-9 expression and activity induced by hyperosmotic stress.

While embodiments of the invention have been illustrated with a limited number of examples. One skilled in the art would appreciate that other modifications or variations are possible without departing from the scope of the invention. Therefore, the scope of protection should be limited by the accompanying claims.

What is claimed is:

1. A pharmaceutical composition for treating dry eye disease in a subject, comprising a peptide and a pharmaceutically acceptable excipient, wherein the peptide comprises a peptide fragment derived from pigment epithelium-derived factor (PEDF) and optionally an N-extension and/or a C-extension that extend, respectively, from an N-terminus and/or a C-terminus of the peptide fragment, wherein the N-extension and the C-extension are not derived from PEDF, wherein the peptide fragment consists of the sequence of S-X-X-A-X-Q/H-X-X-X-X-X I/V-I-X-R (SEQ ID NO:1), wherein each X is independently any naturally-occurring amino acid, provided that the peptide does not comprise the sequence of S-L-G-A-E-Q-R-T-E-S-I-I-H-R (SEQ ID NO:2), S-L-G-A-E-H-R-T-E-S-V-I-H-R (SEQ ID NO:3), S-L-X-A-X-Q/H-X-X-X-X-I/V-I-X-R (SEQ ID NO:6), or S-X-G-A-E-Q/H-R-T-E-S-I/V-I-H-R (SEQ ID NO:74).

2. The pharmaceutical composition according to claim 1, wherein the peptide comprises the sequence of any one of SEQ ID NOs: 7 to 73, and 75.

3. The pharmaceutical composition according to claim 1, wherein the peptide consists of 20, 22, 24, or 29 amino acids in length.

4. The pharmaceutical composition according to claim 1, wherein the peptide is modified with acetylation at the N-terminus or modified with amidation at the C-terminus.

5. The pharmaceutical composition according to claim 1, wherein the dry eye disease is associated with corneal damage.

6. The pharmaceutical composition according to claim 4, wherein a concentration of said peptide is 10 to 200 µM.

7. The pharmaceutical composition according to claim 4, wherein said composition is in a form of a solution, ointment, or gel.

8. The pharmaceutical composition according to claim 4, wherein said subject is a human subject.

9. A method treating dry eye disease, comprising administering to a subject in need thereof a composition comprising a peptide and a pharmaceutically acceptable excipient, wherein the peptide comprises the sequence of S-X-X-A-X-Q/H-X-X-X-X-I/V-I-X-R (SEQ ID NO:1), wherein each X is independently any naturally-occurring amino acid.

10. The method according to claim 9, wherein the dry eye disease is associated with corneal damage.

11. The method according to claim 9, wherein a concentration of said peptide is 10 to 200 µM.

12. The method according to claim 9, wherein said composition is in a form of a solution, ointment, or gel.

13. The method according to claim 9, wherein said subject is a human subject.

14. The method according to claim 9, wherein said peptide comprises the sequence of SLGAEQRTESIIHR (SEQ ID NO:2) or SLGAEHRTESVIHR (SEQ ID NO:3).

15. The method according to claim 9, wherein the peptide comprises the sequence of any one of SEQ ID NOs: 6 to 75.

16. The method according to claim 9, wherein the peptide consists of 20, 22, 24, or 29 amino acids in length.

17. Th method according to claim 9, wherein the peptide is modified with acetylation at the N-terminus or modified with amidation at the C-terminus.

* * * * *

SEQUENCE LISTING

<160> NUMBER OF SEQ ID NOS: 88

<210> SEQ ID NO 1
<211> LENGTH: 14
<212> TYPE: PRT

```
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 1

Ser Xaa Xaa Ala Xaa Xaa Xaa Xaa Xaa Xaa Ile Xaa Arg
1               5                   10

<210> SEQ ID NO 2
<211> LENGTH: 14
<212> TYPE: PRT
<213> ORGANISM: Homo sapiens

<400> SEQUENCE: 2

Ser Leu Gly Ala Glu Gln Arg Thr Glu Ser Ile Ile His Arg
1               5                   10

<210> SEQ ID NO 3
<211> LENGTH: 14
<212> TYPE: PRT
<213> ORGANISM: Mus musculus

<400> SEQUENCE: 3

Ser Leu Gly Ala Glu His Arg Thr Glu Ser Val Ile His Arg
1               5                   10

<210> SEQ ID NO 4
<211> LENGTH: 29
<212> TYPE: PRT
<213> ORGANISM: Homo sapiens

<400> SEQUENCE: 4

Ser Leu Gly Ala Glu Gln Arg Thr Glu Ser Ile Ile His Arg Ala Leu
1               5                   10                  15

Tyr Tyr Asp Leu Ile Ser Ser Pro Asp Ile His Gly Thr
            20                  25

<210> SEQ ID NO 5
<211> LENGTH: 29
<212> TYPE: PRT
<213> ORGANISM: Mus musculus

<400> SEQUENCE: 5

Ser Leu Gly Ala Glu His Arg Thr Glu Ser Val Ile His Arg Ala Leu
1               5                   10                  15

Tyr Tyr Asp Leu Ile Thr Asn Pro Asp Ile His Ser Thr
            20                  25

<210> SEQ ID NO 6
<211> LENGTH: 14
<212> TYPE: PRT
<213> ORGANISM: Artificial Sequence
<220> FEATURE:
<223> OTHER INFORMATION: synthetic
<220> FEATURE:
```

```
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 6

Ser Leu Xaa Ala Xaa Xaa Xaa Xaa Xaa Xaa Xaa Ile Xaa Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 7

Ser Ala Xaa Ala Xaa Xaa Xaa Xaa Xaa Xaa Xaa Ile Xaa Arg
1               5                   10

<210> SEQ ID NO 8
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 8

Ser Xaa Gly Ala Xaa Xaa Xaa Xaa Xaa Xaa Xaa Ile Xaa Arg
1               5                   10

<210> SEQ ID NO 9
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
```

```
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 9

Ser Xaa Ala Ala Xaa Xaa Xaa Xaa Xaa Xaa Xaa Ile Xaa Arg
1               5                   10

<210> SEQ ID NO 10
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 10

Ser Xaa Xaa Ala Glu Xaa Xaa Xaa Xaa Xaa Xaa Ile Xaa Arg
1               5                   10

<210> SEQ ID NO 11
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 11

Ser Xaa Xaa Ala Ala Xaa Xaa Xaa Xaa Xaa Xaa Ile Xaa Arg
1               5                   10

<210> SEQ ID NO 12
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
```

```
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 12

Ser Xaa Xaa Ala Xaa Xaa Arg Xaa Xaa Xaa Xaa Ile Xaa Arg
1               5                   10

<210> SEQ ID NO 13
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 13

Ser Xaa Xaa Ala Xaa Xaa Ala Xaa Xaa Xaa Xaa Ile Xaa Arg
1               5                   10

<210> SEQ ID NO 14
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 14

Ser Xaa Xaa Ala Xaa Xaa Xaa Thr Xaa Xaa Xaa Ile Xaa Arg
1               5                   10

<210> SEQ ID NO 15
<211> LENGTH: 14
<212> TYPE: PRT
<213> ORGANISM: Artificial Sequence
<220> FEATURE:
<223> OTHER INFORMATION: synthetic
<220> FEATURE:
```

```
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 15

Ser Xaa Xaa Ala Xaa Xaa Xaa Ala Glu Xaa Xaa Ile Xaa Arg
1               5                   10

<210> SEQ ID NO 16
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 16

Ser Xaa Xaa Ala Xaa Xaa Xaa Xaa Ala Xaa Xaa Ile Xaa Arg
1               5                   10

<210> SEQ ID NO 17
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 17

Ser Xaa Xaa Ala Xaa Xaa Xaa Xaa Xaa Ser Xaa Ile Xaa Arg
1               5                   10
```

```
<210> SEQ ID NO 18
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 18

Ser Xaa Xaa Ala Xaa Xaa Xaa Xaa Xaa Ala Xaa Ile Xaa Arg
1               5                   10

<210> SEQ ID NO 19
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid

<400> SEQUENCE: 19

Ser Xaa Xaa Ala Xaa Xaa Xaa Xaa Xaa Xaa Xaa Ile His Arg
1               5                   10

<210> SEQ ID NO 20
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid

<400> SEQUENCE: 20

Ser Xaa Xaa Ala Xaa Xaa Xaa Xaa Xaa Xaa Xaa Ile Ala Arg
1               5                   10

<210> SEQ ID NO 21
<211> LENGTH: 14
<212> TYPE: PRT
<213> ORGANISM: Artificial Sequence
<220> FEATURE:
<223> OTHER INFORMATION: synthetic
<220> FEATURE:
```

```
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 21

Ser Leu Gly Ala Xaa Xaa Xaa Xaa Xaa Xaa Xaa Ile Xaa Arg
1               5                   10

<210> SEQ ID NO 22
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 22

Ser Leu Gly Ala Glu Xaa Xaa Xaa Xaa Xaa Xaa Ile Xaa Arg
1               5                   10

<210> SEQ ID NO 23
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 23

Ser Leu Gly Ala Ala Xaa Xaa Xaa Xaa Xaa Xaa Ile Xaa Arg
1               5                   10

<210> SEQ ID NO 24
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 24

Ser Leu Gly Ala Xaa Xaa Arg Xaa Xaa Xaa Xaa Ile Xaa Arg
1               5                   10
```

```
<210> SEQ ID NO 25
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 25

Ser Leu Gly Ala Xaa Xaa Ala Xaa Xaa Xaa Xaa Ile Xaa Arg
1               5                   10

<210> SEQ ID NO 26
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 26

Ser Leu Gly Ala Xaa Xaa Xaa Thr Xaa Xaa Xaa Ile Xaa Arg
1               5                   10

<210> SEQ ID NO 27
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 27

Ser Leu Gly Ala Xaa Xaa Xaa Ala Glu Xaa Xaa Ile Xaa Arg
1               5                   10

<210> SEQ ID NO 28
<211> LENGTH: 14
```

```
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 28

Ser Leu Gly Ala Xaa Xaa Xaa Xaa Ala Xaa Xaa Ile Xaa Arg
1               5                   10

<210> SEQ ID NO 29
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 29

Ser Leu Gly Ala Xaa Xaa Xaa Xaa Xaa Ser Xaa Ile Xaa Arg
1               5                   10

<210> SEQ ID NO 30
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 30

Ser Leu Gly Ala Xaa Xaa Xaa Xaa Xaa Ala Xaa Ile Xaa Arg
1               5                   10

<210> SEQ ID NO 31
<211> LENGTH: 14
<212> TYPE: PRT
<213> ORGANISM: Artificial Sequence
<220> FEATURE:
<223> OTHER INFORMATION: synthetic
```

```
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 31

Ser Leu Gly Ala Xaa Xaa Xaa Xaa Xaa Ser Xaa Ile His Arg
1               5                   10

<210> SEQ ID NO 32
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 32

Ser Leu Gly Ala Xaa Xaa Xaa Xaa Xaa Ala Xaa Ile Ala Arg
1               5                   10

<210> SEQ ID NO 33
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 33

Ser Leu Gly Ala Glu Xaa Xaa Xaa Xaa Xaa Xaa Ile Xaa Arg
1               5                   10

<210> SEQ ID NO 34
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 34

Ser Leu Gly Ala Glu Xaa Arg Xaa Xaa Xaa Xaa Ile Xaa Arg
```

<210> SEQ ID NO 35
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 35

Ser Leu Gly Ala Glu Xaa Ala Xaa Xaa Xaa Xaa Ile Xaa Arg
1               5                   10

<210> SEQ ID NO 36
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 36

Ser Leu Gly Ala Glu Xaa Xaa Thr Xaa Xaa Xaa Ile Xaa Arg
1               5                   10

<210> SEQ ID NO 37
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 37

Ser Leu Gly Ala Glu Xaa Xaa Ala Glu Xaa Xaa Ile Xaa Arg
1               5                   10

<210> SEQ ID NO 38

```
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 38

Ser Leu Gly Ala Glu Xaa Xaa Xaa Ala Xaa Xaa Ile Xaa Arg
1               5                   10

<210> SEQ ID NO 39
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 39

Ser Leu Gly Ala Glu Xaa Xaa Xaa Xaa Ser Xaa Ile Xaa Arg
1               5                   10

<210> SEQ ID NO 40
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 40

Ser Leu Gly Ala Glu Xaa Xaa Xaa Xaa Ala Xaa Ile Xaa Arg
1               5                   10

<210> SEQ ID NO 41
<211> LENGTH: 14
<212> TYPE: PRT
<213> ORGANISM: Artificial Sequence
<220> FEATURE:
```

```
<223> OTHER INFORMATION: synthetic
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 41

Ser Leu Gly Ala Glu Xaa Xaa Xaa Xaa Ser Xaa Ile His Arg
1               5                   10

<210> SEQ ID NO 42
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 42

Ser Leu Gly Ala Glu Xaa Xaa Xaa Xaa Ala Xaa Ile Ala Arg
1               5                   10

<210> SEQ ID NO 43
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 43

Ser Leu Gly Ala Glu Xaa Arg Xaa Xaa Xaa Xaa Ile Xaa Arg
1               5                   10

<210> SEQ ID NO 44
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(13)
```

<223> OTHER INFORMATION: Xaa can be any naturally occurring amino acid

<400> SEQUENCE: 44

Ser Leu Gly Ala Glu Xaa Arg Thr Xaa Xaa Xaa Ile Xaa Arg
1               5                   10

<210> SEQ ID NO 45
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 45

Ser Leu Gly Ala Glu Xaa Arg Ala Xaa Xaa Xaa Ile Xaa Arg
1               5                   10

<210> SEQ ID NO 46
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 46

Ser Leu Gly Ala Glu Xaa Arg Xaa Ala Xaa Xaa Ile Xaa Arg
1               5                   10

<210> SEQ ID NO 47
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(11)

```
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 47

Ser Leu Gly Ala Glu Xaa Arg Xaa Xaa Ser Xaa Ile Xaa Arg
1               5                   10

<210> SEQ ID NO 48
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 48

Ser Leu Gly Ala Glu Xaa Arg Xaa Xaa Ala Xaa Ile Xaa Arg
1               5                   10

<210> SEQ ID NO 49
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 49

Ser Leu Gly Ala Glu Xaa Arg Xaa Xaa Ser Xaa Ile His Arg
1               5                   10

<210> SEQ ID NO 50
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(9)
```

```
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 50

Ser Leu Gly Ala Glu Xaa Arg Xaa Xaa Ala Xaa Ile Ala Arg
1               5                   10

<210> SEQ ID NO 51
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 51

Ser Leu Gly Ala Glu Xaa Arg Thr Xaa Xaa Xaa Ile Xaa Arg
1               5                   10

<210> SEQ ID NO 52
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 52

Ser Leu Gly Ala Glu Xaa Arg Thr Glu Xaa Xaa Ile Xaa Arg
1               5                   10

<210> SEQ ID NO 53
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
```

```
<223> OTHER INFORMATION: Xaa can be any naturally occurring amino acid

<400> SEQUENCE: 53

Ser Leu Gly Ala Glu Xaa Arg Thr Ala Xaa Xaa Ile Xaa Arg
1               5                   10

<210> SEQ ID NO 54
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 54

Ser Leu Gly Ala Glu Xaa Arg Thr Xaa Ser Xaa Ile Xaa Arg
1               5                   10

<210> SEQ ID NO 55
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 55

Ser Leu Gly Ala Glu Xaa Arg Thr Xaa Ala Xaa Ile Xaa Arg
1               5                   10

<210> SEQ ID NO 56
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
```

```
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 56

Ser Leu Gly Ala Glu Xaa Arg Thr Xaa Ser Xaa Ile His Arg
1               5                   10

<210> SEQ ID NO 57
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 57

Ser Leu Gly Ala Glu Xaa Arg Thr Xaa Ala Xaa Ile Ala Arg
1               5                   10

<210> SEQ ID NO 58
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 58

Ser Leu Gly Ala Glu Xaa Arg Thr Glu Ser Xaa Ile Xaa Arg
1               5                   10

<210> SEQ ID NO 59
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
```

```
<223> OTHER INFORMATION: Xaa can be any naturally occurring amino acid

<400> SEQUENCE: 59

Ser Leu Gly Ala Glu Xaa Arg Thr Glu Ala Xaa Ile Xaa Arg
1               5                   10

<210> SEQ ID NO 60
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 60

Ser Leu Gly Ala Glu Xaa Arg Thr Glu Xaa Xaa Ile His Arg
1               5                   10

<210> SEQ ID NO 61
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 61

Ser Leu Gly Ala Glu Xaa Arg Thr Glu Xaa Xaa Ile Ala Arg
1               5                   10

<210> SEQ ID NO 62
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 62

Ser Leu Gly Ala Glu Xaa Arg Thr Glu Ser Xaa Ile Xaa Arg
1               5                   10

<210> SEQ ID NO 63
<211> LENGTH: 14
<212> TYPE: PRT
<213> ORGANISM: Artificial Sequence
```

```
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 63

Ser Leu Gly Ala Glu Xaa Arg Thr Glu Ser Xaa Ile Ala Arg
1               5                   10

<210> SEQ ID NO 64
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 64

Ser Leu Gly Ala Glu Xaa Arg Thr Xaa Ser Xaa Ile His Arg
1               5                   10

<210> SEQ ID NO 65
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 65

Ser Leu Gly Ala Glu Xaa Arg Thr Ala Ser Xaa Ile His Arg
1               5                   10

<210> SEQ ID NO 66
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
```

<222> LOCATION: (11)..(11)
<223> OTHER INFORMATION: Xaa can be any naturally occurring amino acid

<400> SEQUENCE: 66

Ser Leu Gly Ala Glu Xaa Arg Xaa Glu Ser Xaa Ile His Arg
1               5                   10

<210> SEQ ID NO 67
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 67

Ser Leu Gly Ala Glu Xaa Arg Ala Glu Ser Xaa Ile His Arg
1               5                   10

<210> SEQ ID NO 68
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 68

Ser Leu Gly Ala Glu Xaa Xaa Thr Glu Ser Xaa Ile His Arg
1               5                   10

<210> SEQ ID NO 69
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 69

Ser Leu Gly Ala Glu Xaa Ala Thr Glu Ser Xaa Ile His Arg
1               5                   10

<210> SEQ ID NO 70
<211> LENGTH: 14
<212> TYPE: PRT
<213> ORGANISM: Artificial Sequence
<220> FEATURE:
<223> OTHER INFORMATION: synthetic
<220> FEATURE:

```
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 70

Ser Leu Gly Ala Xaa Xaa Arg Thr Glu Ser Xaa Ile His Arg
1               5                   10

<210> SEQ ID NO 71
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 71

Ser Leu Gly Ala Ala Xaa Arg Thr Glu Ser Xaa Ile His Arg
1               5                   10

<210> SEQ ID NO 72
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 72

Ser Leu Xaa Ala Glu Xaa Arg Thr Glu Ser Xaa Ile His Arg
1               5                   10

<210> SEQ ID NO 73
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 73

Ser Leu Ala Ala Glu Xaa Arg Thr Glu Ser Xaa Ile His Arg
1               5                   10
```

```
<210> SEQ ID NO 74
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 74

Ser Xaa Gly Ala Glu Xaa Arg Thr Glu Ser Xaa Ile His Arg
 1               5                  10

<210> SEQ ID NO 75
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 75

Ser Ala Gly Ala Glu Xaa Arg Thr Glu Ser Xaa Ile His Arg
 1               5                  10

<210> SEQ ID NO 76
<211> LENGTH: 20
<212> TYPE: PRT
<213> ORGANISM: homo sapiens

<400> SEQUENCE: 76

Ser Leu Gly Ala Glu Gln Arg Thr Glu Ser Ile Ile His Arg Ala Leu
 1               5                  10                  15

Tyr Tyr Asp Leu
            20

<210> SEQ ID NO 77
<211> LENGTH: 22
<212> TYPE: PRT
<213> ORGANISM: homo sapiens

<400> SEQUENCE: 77

Ser Leu Gly Ala Glu Gln Arg Thr Glu Ser Ile Ile His Arg Ala Leu
 1               5                  10                  15

Tyr Tyr Asp Leu Ile Ser
            20

<210> SEQ ID NO 78
<211> LENGTH: 24
<212> TYPE: PRT
```

<213> ORGANISM: homo sapiens

<400> SEQUENCE: 78

Ser Leu Gly Ala Glu Gln Arg Thr Glu Ser Ile Ile His Arg Ala Leu
1               5                   10                  15
Tyr Tyr Asp Leu Ile Ser Ser Pro
            20

<210> SEQ ID NO 79
<211> LENGTH: 21
<212> TYPE: DNA
<213> ORGANISM: Artificial Sequence
<220> FEATURE:
<223> OTHER INFORMATION: synthetic

<400> SEQUENCE: 79
ctaccttgtt gcctcctctt t                                           21

<210> SEQ ID NO 80
<211> LENGTH: 22
<212> TYPE: DNA
<213> ORGANISM: Artificial Sequence
<220> FEATURE:
<223> OTHER INFORMATION: synthetic

<400> SEQUENCE: 80
gagcagaggt tcagtgatgt ag                                          22

<210> SEQ ID NO 81
<211> LENGTH: 20
<212> TYPE: DNA
<213> ORGANISM: Artificial Sequence
<220> FEATURE:
<223> OTHER INFORMATION: synthetic

<400> SEQUENCE: 81
ggtgtgtgac gttcccatta                                             20

<210> SEQ ID NO 82
<211> LENGTH: 21
<212> TYPE: DNA
<213> ORGANISM: Artificial Sequence
<220> FEATURE:
<223> OTHER INFORMATION: synthetic

<400> SEQUENCE: 82
attgaggtgg agagctttca g                                           21

<210> SEQ ID NO 83
<211> LENGTH: 22
<212> TYPE: DNA
<213> ORGANISM: Artificial Sequence
<220> FEATURE:
<223> OTHER INFORMATION: synthetic

<400> SEQUENCE: 83
gtctgtagct cattctgctc tg                                          22

<210> SEQ ID NO 84
<211> LENGTH: 20
<212> TYPE: DNA
<213> ORGANISM: Artificial Sequence
<220> FEATURE:
<223> OTHER INFORMATION: synthetic

<400> SEQUENCE: 84

```
gaaggcaact ggatggaagt                                              20

<210> SEQ ID NO 85
<211> LENGTH: 21
<212> TYPE: DNA
<213> ORGANISM: Artificial Sequence
<220> FEATURE:
<223> OTHER INFORMATION: synthetic

<400> SEQUENCE: 85
ctcggactgt gatgccttaa t                                            21

<210> SEQ ID NO 86
<211> LENGTH: 21
<212> TYPE: DNA
<213> ORGANISM: Artificial Sequence
<220> FEATURE:
<223> OTHER INFORMATION: synthetic

<400> SEQUENCE: 86
tggatccaca ccttgcattt a                                            21

<210> SEQ ID NO 87
<211> LENGTH: 20
<212> TYPE: DNA
<213> ORGANISM: Artificial Sequence
<220> FEATURE:
<223> OTHER INFORMATION: synthetic

<400> SEQUENCE: 87
tgcgagtttc cgttcatctt                                              20

<210> SEQ ID NO 88
<211> LENGTH: 22
<212> TYPE: DNA
<213> ORGANISM: Artificial Sequence
<220> FEATURE:
<223> OTHER INFORMATION: synthetic

<400> SEQUENCE: 88
gtagagcttg tccttgtcgt ag                                           22
```